United States Patent
Chen et al.

(10) Patent No.: US 8,229,199 B2
(45) Date of Patent: Jul. 24, 2012

(54) METHOD FOR IMAGE RECONSTRUCTION USING SPARSITY-CONSTRAINED CORRECTION

(75) Inventors: Guang-Hong Chen, Madison, WI (US); Shuai Leng, Rochester, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 825 days.

(21) Appl. No.: 12/341,598

(22) Filed: Dec. 22, 2008

(65) Prior Publication Data

US 2009/0175523 A1 Jul. 9, 2009

Related U.S. Application Data

(60) Provisional application No. 61/020,847, filed on Jan. 14, 2008, provisional application No. 61/059,891, filed on Jun. 9, 2008, provisional application No. 61/015,559, filed on Dec. 20, 2007.

(51) Int. Cl.
*G06K 9/00* (2006.01)
(52) U.S. Cl. ......... 382/130; 382/128; 382/131; 382/132
(58) Field of Classification Search .................. 382/128, 382/129, 130, 131, 132, 133, 134
See application file for complete search history.

(56) References Cited

U.S. PATENT DOCUMENTS

| | | | |
|---|---|---|---|
| 4,878,169 A | 10/1989 | Toner et al. | |
| 6,841,998 B1 | 1/2005 | Griswold | |
| 7,289,049 B1 | 10/2007 | Fudge et al. | |
| 7,330,027 B2 | 2/2008 | Kozerke et al. | |
| 7,358,730 B2 * | 4/2008 | Mistretta et al. | 324/307 |
| 7,408,347 B2 | 8/2008 | Mistretta et al. | |
| 7,519,412 B2 * | 4/2009 | Mistretta | 600/407 |
| 7,545,901 B2 * | 6/2009 | Mistretta | 378/4 |
| 7,558,414 B2 | 7/2009 | Griswold | |
| 7,647,088 B2 * | 1/2010 | Mistretta et al. | 600/428 |
| 2006/0029279 A1 | 2/2006 | Donoho | |
| 2007/0010731 A1 * | 1/2007 | Mistretta | 600/407 |
| 2007/0038073 A1 * | 2/2007 | Mistretta | 600/410 |
| 2007/0106149 A1 | 5/2007 | Mistretta | |
| 2007/0156044 A1 * | 7/2007 | Mistretta et al. | 600/410 |
| 2007/0167707 A1 * | 7/2007 | Mistretta et al. | 600/407 |
| 2007/0167728 A1 | 7/2007 | Mistretta et al. | |
| 2007/0167729 A1 | 7/2007 | Mistretta et al. | |
| 2008/0199063 A1 * | 8/2008 | O'Halloran et al. | 382/131 |
| 2008/0219535 A1 | 9/2008 | Mistretta et al. | |
| 2009/0076369 A1 | 3/2009 | Mistretta | |

(Continued)

OTHER PUBLICATIONS

Kevin M. Johnson, Julia Velikina, Yijing Wu, Steve Kecskenmeti, Oliver Wieben and Charles Mistretta, "Improved Waveform Fidelity Using Local HYPR Reconstruction (HYPR LR)," 2008, Magnetic Resonance in Medicine 59:456-462.*

(Continued)

*Primary Examiner* — Francis M Legasse, Jr.
*Assistant Examiner* — Bao-Luan Le
(74) *Attorney, Agent, or Firm* — Quarles & Brady LLP

(57) ABSTRACT

An image reconstruction method applicable to a number of different imaging modalities including magnetic resonance imaging (MRI), x-ray computed tomography (CT), positron emission tomography (PET), and single photon emission computed tomography (SPECT) is disclosed. A sparsifying image is reconstructed from a series of acquired undersampled data to provide a priori knowledge of a subject being imaged. An iterative reconstruction process is further employed to iteratively determine a correction image for a given image frame that, when subtracted from the sparsifying image, produces a quality image for the image frame.

9 Claims, 15 Drawing Sheets

U.S. PATENT DOCUMENTS

2009/0129651 A1  5/2009  Zagzebski et al.
2010/0177949 A1* 7/2010  Sakai .......................... 382/132

OTHER PUBLICATIONS

Seung-Jean Kim, Kwangmoo Koh, Michael Lustig and Stephen Boyd, "An Efficient Method for Compressed Sensing," 2007, IEEE, III-117-III-120.*

Samsonov A. A., Wieben O and Block W. F., "HYPRIT: Generalized HYPR Reconstruction by Iterative Estimation," 2007, ISMRM workshop on Non-Cartesian Imaging.*

Michael Lustig, Student Member, IEEE; Compressed Sensing MRI; 18 pages; 2007.

Kathryn L Garden et al; 3-D Reconstruction of the Heart From Few Projections: A Practical Implementation of the McKinnon-Bates Algorithm; IEEE Transactions on Medical Imaging, vol. MI-5, No. 4, Dec. 1986.

Graeme C McKinnon et al; Towards Imaging the Beating Heart Usefully With a Conventional CT Scanner; IEEE Transactions on Biomedical Engineering, vol. BME-28, No. 2, Feb. 1981.

Jiayu Song et al; Sparseness Prior Based Iterative Image Reconstruction for Retrospectively Gated Cardiac Micro-CT; Med. Phys. 34(11), Nov. 2007; pp. 4476-4483.

M. Lustig, et al., "Sparse MRI: The application of compressed sensing for rapid MR imaging" Magnetic Resonance in Medicine 58(6):1182-1195 (2007).

David L Donoho, member IEEE; Compressed Sensing; IEEE Transactions on Information Theory, vol. 52, No. 4, Apr. 2006; 1289-1306.

Emmanuel J Cades et al; Robust Uncertainty Principles: Exact Signal Reconstruction From Highly Incomplete Frequency Information; IEEE Transactions on Information Theory, vol. 22, No. 2, Feb. 2006; 489-509.

Steffen Weiss et al; Projection-Reconstruction Reduces FOV Imaging; Magnetic Resonance Imaging, vol. 17, No. 4, pp. 517-515, 1999.

Fessler, et al., "Iterative Image Reconstruction in MRI With Separate Magnitude and Phase Regularization," IEEE International Symposium on Biomedical Imaging: Nano to Macro, 2004; 1:209-212.

Lustig, et al., "Rapid MR Imaging with 'Compressed Sensing' and Randomly Under-Sampled 3DFT Trajectories", Proc. Intl. Soc. Mag. Reson. Med. 14 (2006), p. 695.

Mistretta, et al., "Highly Constrained Backprojection for Time-Resolved MRI", Magn Reson Med, 2006, 55(1):30-40.

Donoho, "Compressed Sensing", Sep. 14, 2004, pp. 1-34.

Schmidt, "Least Squares Optimization with L1-Norm Regularization", Dec. 2005, pp. 1-12.

O'Halloran, et al., "Iterative Projection Reconstruction of Time-Resolved Images Using Highly-Constrained Back-Projection (HYPR)", Magn Reson Med, 2008, 59:132-139 (published online Dec. 3, 2007).

* cited by examiner

METHOD FOR IMAGE RECONSTRUCTION USING SPARSITY-CONSTRAINED CORRECTION

CROSS-REFERENCE TO RELATED APPLICATIONS

This application claims the benefit of U.S. Provisional Patent Application Ser. No. 61/015,559 filed on Dec. 20, 2007 and entitled "Method for Image Reconstruction Using Prior Image Constrained Compressed Sensing"; U.S. Provisional Patent Application Ser. No. 61/020,847 filed on Jan. 14, 2008 and entitled "Method for Image Reconstruction Using Prior Image Constrained Compressed Sensing"; and U.S. Provisional Patent Application Ser. No. 61/059,891 filed on Jun. 9, 2008 and entitled "Method for Image Reconstruction Using Prior Image Constrained Compressed Sensing".

STATEMENT REGARDING FEDERALLY SPONSORED RESEARCH

This invention was made with United States government support awarded by the following agencies: and NIH EB007021. The United States government has certain rights in this invention.

BACKGROUND OF THE INVENTION

The field of the invention is medical imaging and particularly, methods for reconstructing images from acquired image data.

In a computed tomography system, an x-ray source projects a cone-shaped beam which is collimated to lie within an x-y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile," or "attenuation profile," or "projection."

The source and detector array in a conventional CT system are rotated on a gantry within the imaging plane and around the object so that the angle at which the x-ray beam intersects the object constantly changes. The transmission profile from the detector array at a given angle is referred to as a "view," and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This image reconstruction process converts the attenuation measurements acquired during a scan into integers called "CT numbers" or "Hounsfield units", which are used to control the brightness of a corresponding pixel on a display.

Radiation therapy is a treatment technique that delivers radiation to a defined target volume in a subject. The radiation is delivered in such a manner that the surrounding healthy tissue does not receive radiation doses in excess of allowed tolerances. In order to achieve this control of the imparted dose to the subject, highly accurate radiation delivery techniques are required. Many factors provide difficulties in obtaining the desired level of accuracy, including differences between the planned and delivered dose distributions and uncertainty in subject position with respect to the treatment system.

Intensity modulation radiation therapy ("IMRT") is a radiation therapy technique that utilizes computer planning software to produce a three-dimensional radiation dose map, specific to a target tumor's shape, location, and motion characteristics. Because of the high level of precision required for IMRT methods, detailed data must be gathered about tumor locations and their motion characteristics. In doing so, the radiation dose imparted to healthy tissue can be reduced while the dose imparted to the affected region, such as a tumor, can be increased. In order to achieve this, accurate geometric precision is required during the treatment planning stage.

Image-guided radiation therapy ("IGRT") employs medical imaging, such as computed tomography (CT), concurrently with the delivery of radiation to a subject undergoing treatment. In general, IGRT is employed to accurately direct radiation therapy using positional information from the medical images to supplement a prescribed radiation delivery plan. The advantage of using IGRT is twofold. First, it provides a means for improved accuracy of the radiation field placement. Second, it provides a method for reducing the dose imparted to healthy tissue during treatment. Moreover, the improved accuracy in the delivery of the radiation field allows for dose escalation in the tumor, while mitigating dose levels in the surrounding healthy tissue. Exemplary IGRT methods include the use of two- and three-dimensional imaging techniques. Additionally, so-called "four-dimensional" imaging techniques, in which a time series of three-dimensional images are obtained, may be employed during IGRT. In three-dimensional IGRT, imaging is performed using cone-beam computed tomography ("CBCT"), while in two-dimensional IGRT, planar digital radiographs, fluoroscopy image frames, or megavoltage (MV) images are matched with digital reconstructed radiographs (DRRs) from the radiation delivery plan. Recently developed CBCT based IGRT systems include systems where a CBCT is integrated with medical linear accelerator. With improvements in flat-panel technology, CBCT has been able to provide volumetric imaging, and allows for radiographic or fluoroscopic monitoring throughout the treatment process.

SUMMARY OF THE INVENTION

The present invention provides an image reconstruction method applicable to a number of different imaging modalities including magnetic resonance imaging (MRI), x-ray computed tomography (CT), positron emission tomography (PET), and single photon emission computed tomography (SPECT). In this method, a sparsifying image is reconstructed from acquired data to provide a priori knowledge of the subject being imaged. An iterative reconstruction process is employed to iteratively determine a correction image for a given image frame that when subtracted from the sparsifying image produces a quality image for the image frame.

A general aspect of the invention is to improve the reconstruction of medical images by constraining the reconstruction process with a priori information regarding the subject of the image. A sparsifying image is reconstructed from a series of acquired undersampled image data sets and is employed to produce quality images from the undersampled data sets. Correction images are produced for each image data set from which a quality image is sought to be produced. Each of said images is subsequently produced by subtracting the corresponding correction image from the sparsifying image. The improvement resulting from the present invention can manifest itself in a number of ways, including reduction of scan time, reduction in radiation dose, and higher temporal resolution in time-resolved studies.

Another aspect of the invention is to improve the quality of previously reconstructed images in a series of images having poor quality. A plurality of image data sets are produced by reprojecting the corresponding images into x-ray projection space, and a sparsifying image is produced therefrom. An iterative reconstruction process is employed to produce a correction image corresponding to one of the image data sets. This correction image is subsequently subtracted from the sparsifying image to produce a higher quality version of the corresponding original image. This process is repeated for each image in the series of original, lower quality, images.

Yet another aspect of the present invention provides a method for more accurately adjusting the delivery of radiation to a medical patient through improved image-guided radiation therapy (IGRT). A prior image is reconstructed from image data acquired contemporaneously with a signal indicative of the medical patient's respiration. The prior image is reconstructed using a composite, or "sparsifying" image reconstructed from the acquired image data and from projection views acquired during a given respiratory phase, or a so-called "respiratory phase image data set." In this manner, the prior image contains information regarding the specific respiratory phase for which a desired image is reconstructed. In this manner, the motion characteristics of a tumor can be more accurately determined, and the radiation delivery plan adjusted accordingly.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
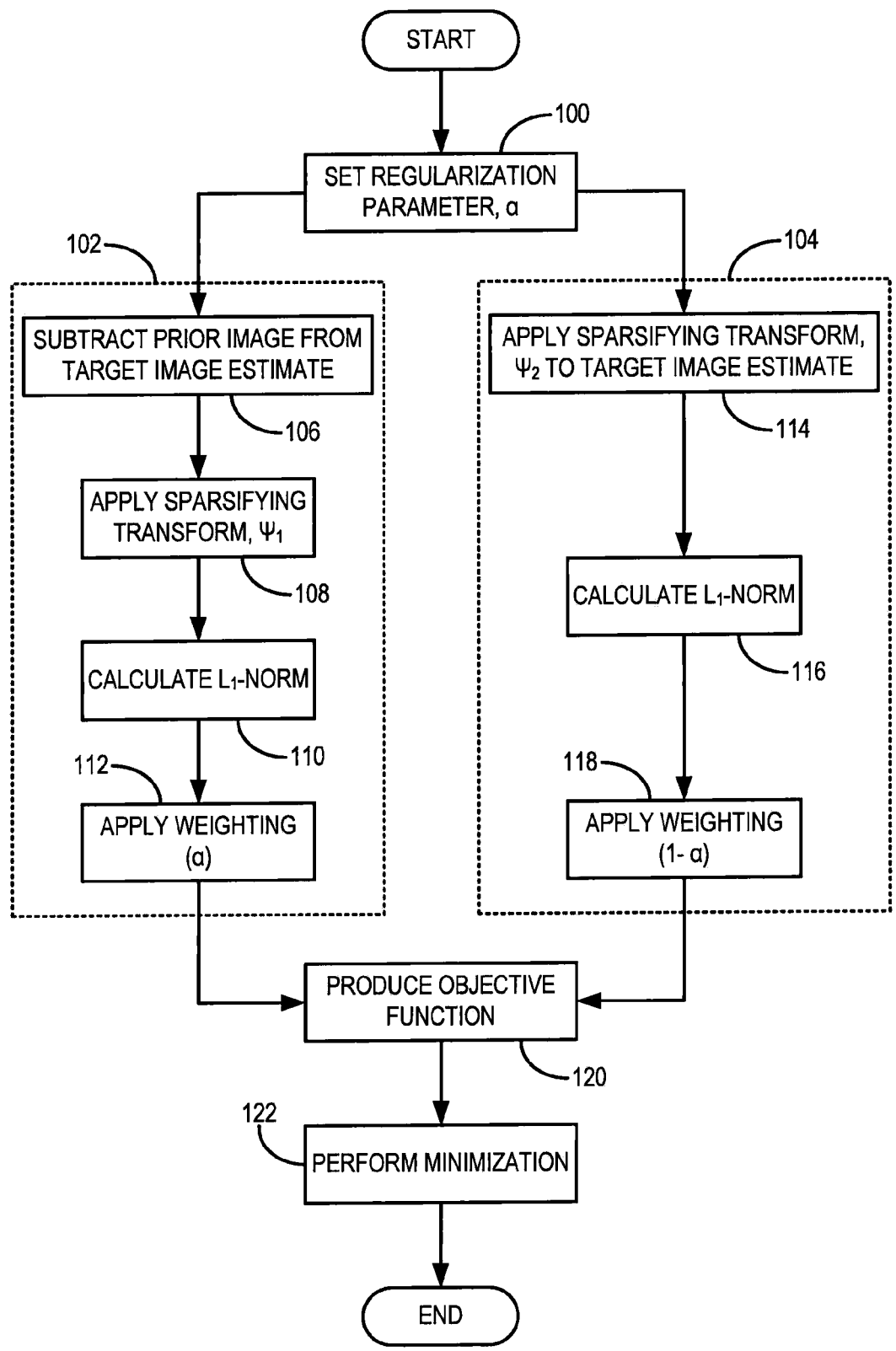
FIG. 1 is a flowchart an embodiment of an image reconstruction method employed when practicing the present invention.

Generally speaking, the method of reconstructing an image from a set of data includes a series of numerical steps to estimate a desired image, I, from the measured data samples, Y. More specifically, the image reconstruction should fulfill the following consistency condition:

$$AI=Y \qquad \text{Eqn. (1)};$$

where A is a system matrix. In general, the system matrix, A, can be viewed as a forward projection operator that relates the desired image, I, to the acquired data samples, Y. When dealing with computed tomography (CT) imaging, for example, the system matrix can include a reprojection operation. The consistency condition of equation (1), put in other words, states that when an image is faithfully reconstructed, the forward operation should substantially mimic the actual data acquisition procedure in order to generate a correct estimate of the measured projection data.

Turning now to an exemplary image reconstruction method employed when practicing the present invention, a method for reconstructing a quality desired image from less image data than typically required is provided. In general, a "prior image" is employed to constrain an iterative image reconstruction method, in which the principles of compressed sensing (CS) are utilized. For example, in addition to the sparsifying transforms commonly used in CS, an image is further sparsified by subtracting the prior image from the desired image. As a result, an image can be accurately reconstructed using a substantially fewer number of samples than required by CS methods.

More specifically, given a prior image, $I_P$, and a desired image to be reconstructed, I, the exemplary image reconstruction method employed when practicing the present invention is implemented by minimizing the following objective function:

$$\alpha\|\Psi_1(I-I_P)\|_1 + (1-\alpha)\|\Psi_2 I\|_1 \qquad \text{Eqn. (2)};$$

where $\Psi_1$ and $\Psi_2$ are sparsifying transforms, $\|\ldots\|_1$ is an $L_1$-norm operation, and $\alpha$ is a regularization parameter that is utilized to control the relative weight of the two terms in the objective function of equation (2). As noted above, the following:

$$\|x\|_1 = \sum_{i=1}^{N} |x_i|; \qquad \text{Eqn. (3)}$$

indicates the $L_1$-norm of an N-dimensional vector, x. More generally, a deviation from the true $L_1$-norm is possible while still maintaining adequate image quality in the desired image. For example, the objective function of equation (2) can be generalized as:

$$\alpha \|\Psi_1(I-I_P)\|_p + (1-\alpha)\|\Psi_2 I\|_p \qquad \text{Eqn. (4)};$$

where $\|\ldots\|_p$ is an $L_p$-norm operation having the form:

$$\|x\|_p = \left( \sum_{i=1}^{N} |x_i|^p \right)^{1/p}. \qquad \text{Eqn. (5)}$$

As noted above, preferably p=1.0; however, in the alternative, different values of p are possible. It should be appreciated by those skilled in the art that the further the value of p deviates from p=1.0, generally, the more degradation will be evident in the reconstructed desired image.

The sparsifying transforms in equation (2), $\Psi_1$ and $\Psi_2$, are, in general, different; however, in the alternative, $\Psi_1$ and $\Psi_2$ may be the same sparsifying transform. Exemplary sparsifying transforms include a wavelet transform, a first order finite difference, a second order finite difference, and a discrete gradient transform, such as, for example, a discrete gradient transform, $\nabla_{m,n}$, having the following form:

$$\nabla_{m,n} I(m,n) = \sqrt{\begin{array}{l}[I(m+1,n)-I(m,n)]^2 + \\ [I(m,n+1)-I(m,n)]^2\end{array}}; \qquad \text{Eqn. (6)}$$

where the indices m and n indicate the location of a pixel in an image, I. The image specified as $\nabla_{m,n}I(m,n)$ is commonly referred to as the "gradient image".

Both of the terms in the objective function of equation (2) are important. As a result of their importance, the selection of the regularization parameter, α, is utilized to control the overall image reconstruction process. Therefore, the selection of the regularization parameter, α, will depend on the choice of the prior image, $I_P$, and also the clinical application at hand. For example, the second term in the objective function of equation (2), $(1-\alpha)\|\Psi_2 I\|_1$, mitigates streaking artifacts that are potentially inherited from the prior image, $I_P$. For further example, selecting a regularization parameter of α√0.3-0.7 is generally sufficient for respiratory imaging applications.

To better incorporate the consistency condition of equation (1) into the overall image reconstruction, the method of Lagrange multipliers is utilized. In such a manner, the consistency condition is employed to add a further constraint on the minimization of the objective function set forth in equation (2). A new objective function is thus produced, which has the form:

$$\alpha \|\Psi_1(I-I_P)\|_1 + (1-\alpha)\|\Psi_2 I\|_1 + \lambda \|X\|_2^2 \qquad \text{Eqn. (7)};$$

where λ is the Lagrange multiplier, X is a difference matrix, and $\|\ldots\|_2^2$ is a squared $L_2$-norm operation, which, for an N-dimensional vector, x, has the form:

$$\|x\|_2^2 = \sum_{i=1}^{N} x_i^2. \qquad \text{Eqn. (8)}$$

The difference matrix in equation (7) accounts for the consistency condition of equation (1), and has the following form:

$$X = AI - Y \qquad \text{Eqn. (9)}.$$

The Lagrange multiplier, λ, is determined empirically for the particular imaging system employed when practicing the present invention. For example, the Lagrange multiplier, λ, is determined by a pre-determined tradeoff between the desired data consistency requirement and the similarity to the prior image, $I_P$. When a large Lagrange multiplier, λ, is selected, the reconstructed image has lower noise variance; however, this may be achieved as a loss of the high spatial resolution characteristic of the prior image. Similarly, when a smaller Lagrange multiplier, λ, is used, the high spatial resolution characteristic of the prior image is well preserved, but the noise variance can be high in the desired image. Such a situation affects the contrast-to-noise ratio achievable by the imaging system utilized.

The objective function presented in equation (7) can further be altered in order to account for noise of the imaging system. In such a manner, the following objective function is minimized:

$$\alpha \|\Psi_1(I-I_P)\|_1 + (1-\alpha)\|\Psi_2 I\|_1 + \lambda (X^T D X) \qquad \text{Eqn. (10)};$$

where $X^T$ is the transpose of the difference matrix, X, and D is a system noise matrix, which is a diagonal matrix having the following matrix elements:

$$D_{ij} = \begin{cases} \dfrac{1}{\sigma_n^2} & \text{if } i = j \\ 0 & \text{if } i \neq j; \end{cases} \qquad \text{Eqn. (11)}$$

where $\sigma_n^2$ is the noise variance, and is a parameter indicative of noise in the particular imaging system employed when practicing the present invention. For example, in an x-ray imaging system, the noise parameter, $\sigma_n^2$, is the noise variance associated with the $n^{th}$ x-ray detector.

With reference now to FIG. 1, one implementation of the aforementioned image reconstruction method employs the objective function of equation (2), and begins by initializing the regularization parameter, α, as indicated at step 100. The choice of the regularization parameter, α, determines the trade-off between the sparsity of the desired image, and the influence of the prior image on the desired image. Accordingly, the value of the regularization parameter, α, will vary depending on the clinical application at hand. For example, a value of α≈0.3-0.7 is generally sufficient for respiratory imaging applications. Subsequently, the first and second terms in the objective function of equation (2) are initialized, as indicated in steps 102 and 104, respectively. The initialization of the first term, $\alpha\|\Psi_1(I-I_P)\|_1$, begins at step 106 where the prior image, $I_P$, is subtracted from an estimate of the desired image, I, to produce a "difference image". The particular choice of the prior image, $I_P$, and the estimate of the desired image, I, will depend on the imaging modality and the particular clinical application. Accordingly, different alternatives for these choices will be discussed in detail below. The difference image is subsequently sparsified by applying the sparsifying transform, $\Psi_1$, as indicated at step 108. As described above, the sparsifying transform, $\Psi_1$, can be any number of mathematical operations, including a wavelet transform, a first order finite difference, a second order finite difference, and a discrete gradient transform. The $L_1$-norm of this sparsified difference image is then calculated at step 110.

The result of this process is then weighted by the regularization parameter, α, as indicated at step 112.

The initialization of the second term in the objective function of equation (2), $(1-\alpha)\|\Psi_2 I\|_1$, begins at step 114 where the estimate of the desired image, I, is sparsified through the application of the sparsifying transform, $\Psi_2$. Subsequently, the $L_1$-norm of this sparsified desired image estimate is calculated at step 116. When the discrete gradient transform, $\nabla_{m,n}$, is selected as the sparsifying transform, $\Psi_2$, steps 114 and 116 can be viewed as calculating the total variation, TV, of the desired image estimate, which has the form:

$$TV(I) = \|\nabla I\|_1 = \Sigma |\nabla I| \qquad \text{Eqn. (12).}$$

After the $L_1$-norm of the sparsified desired image estimate is calculated, the result is weighted by $(1-\alpha)$, as indicated at step 118. The objective function of equation (2) is subsequently produced in step 120 by adding the first and second terms together. This objective function is then minimized, as indicated at step 122, using, for example, a nonlinear conjugate gradient method. The minimization process proceeds until a stopping criterion is satisfied. The stopping criterion includes, for example, comparing the current estimate of the desired image with the estimate of the desired image from the previous iteration. Such a stopping criterion has the following form:

$$\sum_i \sum_j (I_{ij}^{(k+1)} - I_{ij}^{(k)})^2; \qquad \text{Eqn. (13)}$$

where, $I_{ij}^{(k+1)}$ is the value of the $(k+1)^{th}$ estimate of the desired image at the pixel location (i,j), and $I_{ij}^{(k)}$ is the value of the $k^{th}$ estimate of the desired image at the pixel location (i,j).

Figure 2:
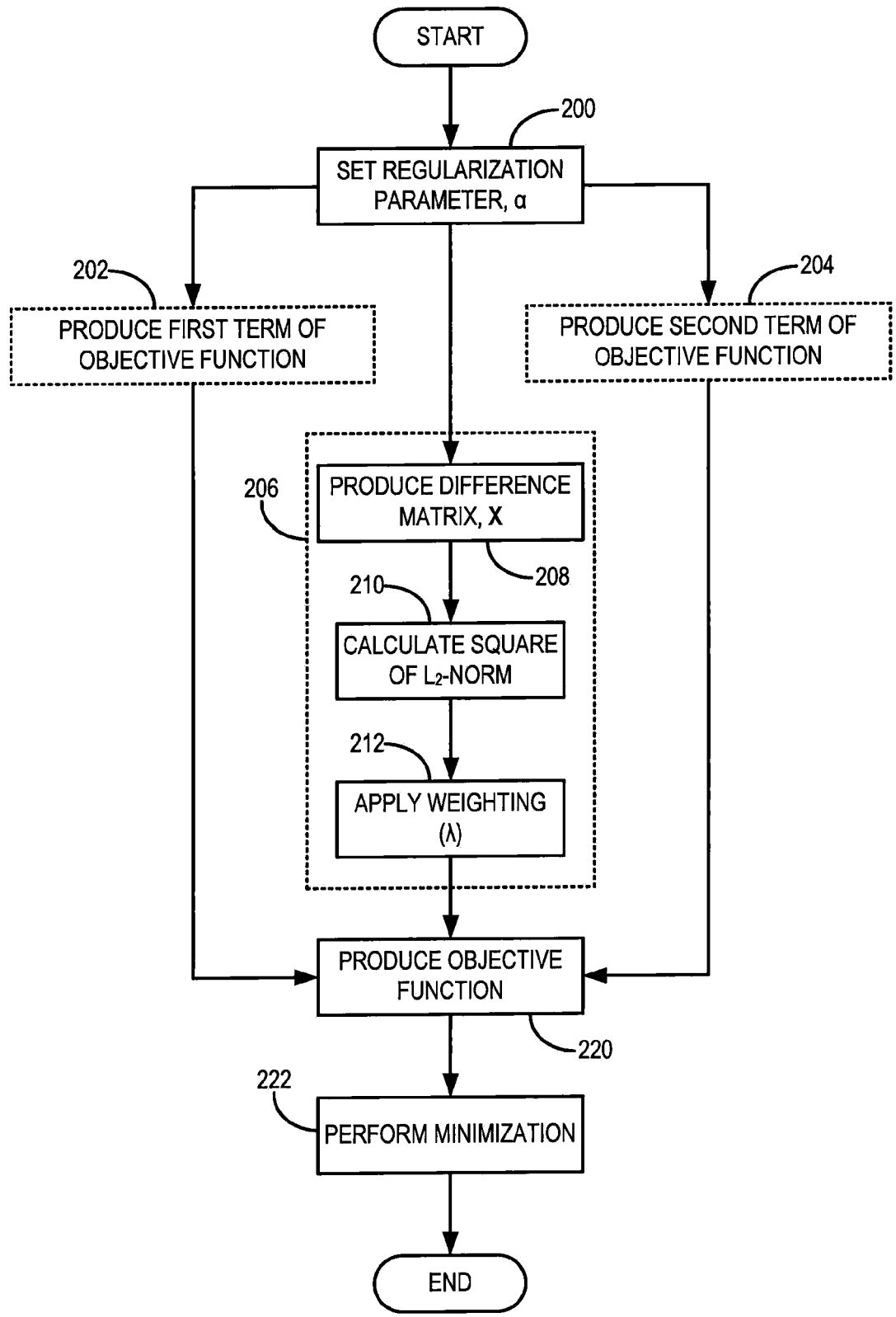
FIG. 2 is a flowchart of another embodiment of an image reconstruction method employed when practicing the present invention.

With reference now to FIG. 2, another implementation of the aforementioned image reconstruction method employs the objective function of equation (7), and begins by initializing the regularization parameter, α, as indicated at step 200. Subsequently, the first and second terms in the objective function of equation (7) are initialized, as indicated in steps 202 and 204, respectively. This process proceeds in the same manner as described above with reference to steps 102 and 104 in FIG. 1. Now, however, the consistency condition of equation (1) is incorporated into a third term, $\lambda \|X\|_2^2$, which is initialized at step 206. First, the difference matrix, X, is produced, as indicated at step 208. As described above in detail, the difference matrix, X, corresponds to the consistency condition of equation (1) and has the form of equation (9).

Thus, the difference matrix is determined by applying the system matrix, A, to the estimate of the desired image, I, and subsequently subtracting the acquired image data, Y, that corresponds to the desired image. The square of the $L_2$-norm of the difference matrix, X, is calculated next at step 210. After the square of the $L_2$-norm of the difference matrix, X, has been produced, the Lagrange multiplier, λ, is determined and employed to weight the difference matrix, X, as indicated at step 212. As described above, the Lagrange multiplier is empirically determined by and the value selected by the user based on the clinical application at hand. The objective function of equation (7) is subsequently produced in step 220 by adding the first, second, and third terms together. This objective function is then minimized, as indicated at step 222, using, for example, a nonlinear conjugate gradient method. The minimization process proceeds until a stopping criterion is satisfied, as described above.

Figure 3:
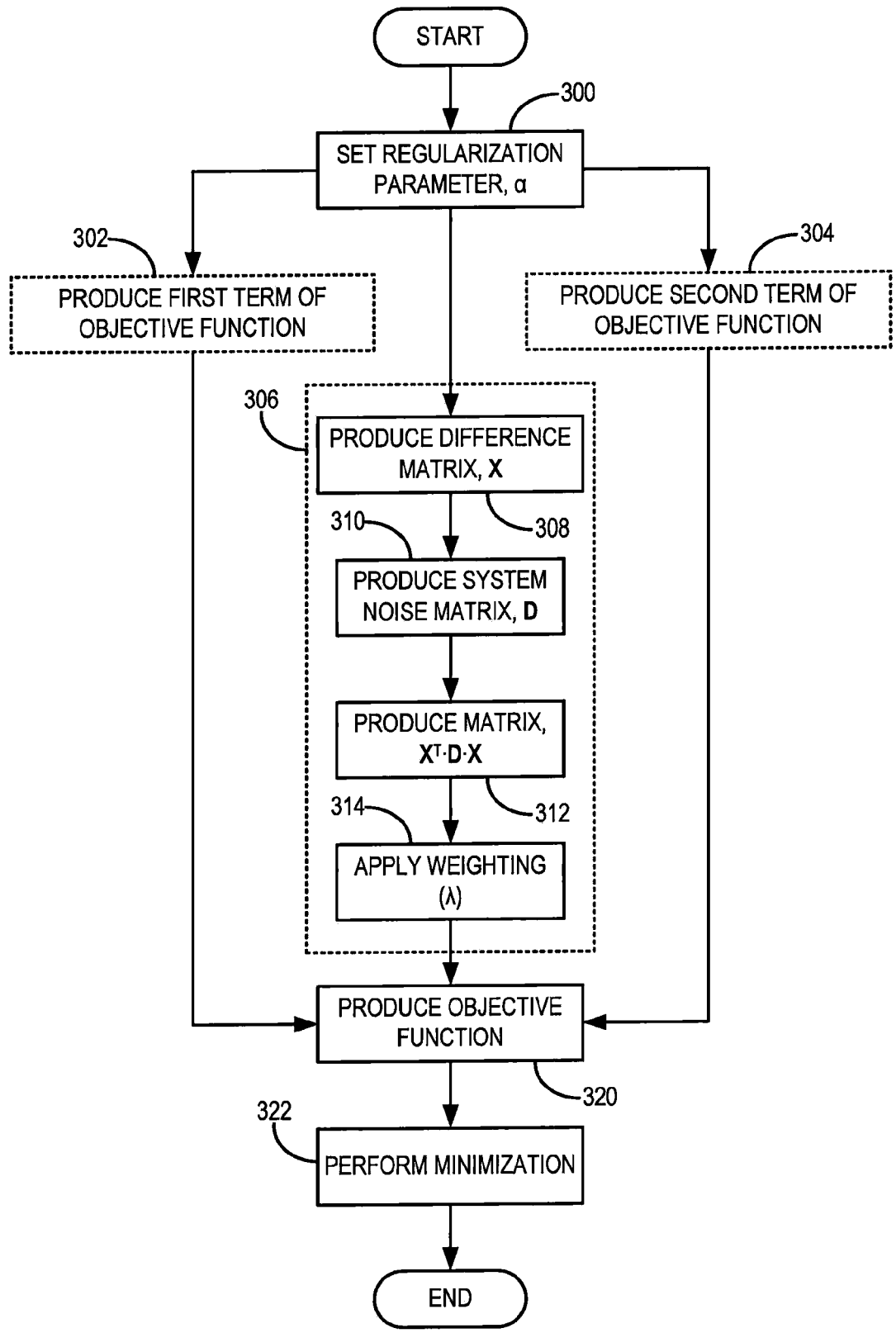
FIG. 3 is a flowchart of yet another embodiment of an image reconstruction method employed when practicing the present invention.

With reference now to FIG. 3, yet another implementation of the aforementioned image reconstruction method employs the objective function of equation (10), and begins by initializing the regularization parameter, α, as indicated at step 300. Subsequently, the first and second terms in the objective function of equation (10) are initialized, as indicated in steps 302 and 304, respectively. This process proceeds in the same manner as described above with reference to steps 102 and 104 in FIG. 1. Now, however, the consistency condition of equation (1) and the effects of noise in the imaging system are incorporated into a third term, $\lambda(X^T D X)$, which is initialized at step 306. First, the difference matrix, X, is produced, as indicated at step 308, and described above with reference to step 208 in FIG. 2. Next, a system noise matrix, D, is produced, as indicated in step 310. The system noise matrix, D, is a diagonal matrix having matrix elements determined in accordance with the following:

$$D_{ij} = \begin{cases} \dfrac{1}{\sigma_n^2} & \text{if } i = j \\ 0 & \text{if } i \neq j. \end{cases} \qquad \text{Eqn. (14)}$$

As described above, $\sigma_n^2$ is the noise variance, and is a parameter indicative of noise in the imaging system employed when practicing the present invention. For example, in an x-ray imaging system, the noise parameter, $\sigma_n^2$, is the noise variance associated with the $n^{th}$ x-ray detector. After the system noise matrix, D, has been produced, the following matrix multiplication is performed:

$$X^T D X, \qquad \text{Eqn. (15);}$$

as indicated at step 312. The result of this operation is subsequently scaled by the Lagrange multiplier, as indicated at step 314. The objective function of equation (10) is subsequently produced in step 320 by adding the first, second, and third terms together. This objective function is then minimized, as indicated at step 322, using, for example, a nonlinear conjugate gradient method. The minimization process proceeds until a stopping criterion is satisfied, as described above.

To estimate the underlying image I from an incomplete dataset along compressed sensing guidelines, the following problem is solved:

$$\min_I \{\|AI - Y\|_2^2 + \lambda \|\Psi I\|_1\}; \qquad \text{Eqn. (16)}$$

where A is the encoding matrix, Y is a vector containing the image data acquired with the imaging system, λ is a control parameter that balances the residual error of the minimization process and the sparsity of the image I, and Ψ is a sparsifying matrix. The sparsifying matrix, Ψ, can be any number of matrices that operate to sparsify an object. In the alternative, Ψ can be the identity matrix. For image data that is acquired with radial sampling projections (e.g., radial MRI, computed tomography, positron emission tomography) the encoding matrix A is the Radon transform matrix and Y is a vector containing Radon space values. In the alternative, if the image data is k-space data that is either initially acquired in a Cartesian sampling pattern or non-Cartesian k-space samples regridded to a Cartesian grid, A is the Fourier transform matrix and Y is a vector containing k-space values. The image, Y, is the underlying image sought to be reconstructed.

Often, data are sampled in a temporal or parametric dimension and possess a significant degree of redundancy, as image pixels may highly correlate along such a dimension. For example, the background tissues in a time-resolved angiographic imaging study will contain substantially the same pixel information. Likewise, in diffusion studies, gray matter exhibits substantially isotropic diffusion behavior and thus, gray matter pixels for different diffusion gradient directions will be highly correlated. This property can be exploited in the compressed sensing framework through the following:

$$\min_I \{\|AI - Y\|_p + \lambda\|\Psi(I - I_s)\|_1\}; \qquad \text{Eqn. (17)}$$

where $I_s$ is a sparsifying image which is a reasonable estimate of image intensity distribution and $\|\ldots\|_p$ is the p-norm, which for an arbitrary vector x with length K has the form:

$$\|x\|_p = \left(\sum_{k=1}^{K} |x_k|^p\right)^{\frac{1}{p}}; \qquad \text{Eqn. (18)}$$

and where $0 \leq p \leq \infty$.

The sparsifying image, $I_s$, may be produced by a number of different methods including but not limited to a sliding window reconstruction. In the alternative, the sparsifying image can be reconstructed using other image reconstruction methods such as, for example, HYPR, which is described in co-pending U.S. patent application Ser. No. 11/482,372; HYPR-LR, which is described in co-pending U.S. patent application Ser. No. 12/032,240; and I-HYPR, which is described in co-pending U.S. patent application Ser. No. 12/032,262. By employing the HYPR-LR method, for example, a further increase in the signal-to-noise ratio (SNR) is possible in the desired image frame.

As an example, consider a series of undersampled data sets acquired with a medical imaging system over a period of time, such that a dynamic process is imaged. An exemplary situation could be a series of image data sets acquired during the passage of a contrast agent through the vasculature of a patient. Each individual image data set can be reconstructed to produce an image frame; however, these image frames will be of poor quality as a result of undersampling artifacts. In this situation, a sparsifying image, $I_s$, can be reconstructed from a plurality of the image data sets to produce a reasonable representation of the image intensity throughout the series of image frames. In order to reconstruct a quality image frame, equation (17) above can be employed in an iterative reconstruction method to produce a correction image indicative of the information present in the sparsifying image that does not form a part of the desired underlying image frame. In this manner, equation (17) is rewritten as:

$$\min_{I_{corr}} \{\|Y_{corr} - AI_{corr}\|_p + \lambda\|\Psi I_{corr}\|_1\}; \qquad \text{Eqn. (19)}$$

where:

$Y_{corr} = AI_s - Y$ is a vector containing corrected image data; and $I_{corr} = I_s - I$ is the correction image. Therefore, by iteratively minimizing equation (19), a correction image, $I_{corr}$, is produced that when subtracted from the sparsifying image, $I_s$, results in a quality estimate of the desired underlying image frame, I. Other minimization methods similar to the one described in equation (19) can further be employed to practice the present invention. Such an exemplary minimization method includes:

$$\min_{I_{corr}} \{\|Y_{corr} - AI_{corr}\|_2^2 + \lambda\|\Psi I_{corr}\|_q^q\}; \qquad \text{Eqn. (20)}$$

Where $1 \leq q \leq 2$, and $(\ldots)^q$ indicates the conventional $q^{th}$ power operation.

The present invention may be applied to many different medical imaging modalities and to many different clinical applications. A number of these clinical applications of the invention are described below to illustrate the broad scope of the present invention. While the preferred embodiment of the present invention is to reconstruct an image from data acquired with a medical imaging system, it should be appreciated to those skilled in the art that it is possible to use the present invention to improve the quality of existing images. Such existing images may be decomposed into a set of projection views and a new image can be reconstructed from them using the reconstruction method of the present invention. The improvement will depend, of course, on the quality of the sparsifying image that is used, and this in turn will depend on the available a priori information regarding the subject being imaged.

Magnetic Resonance Imaging System

Figure 4:
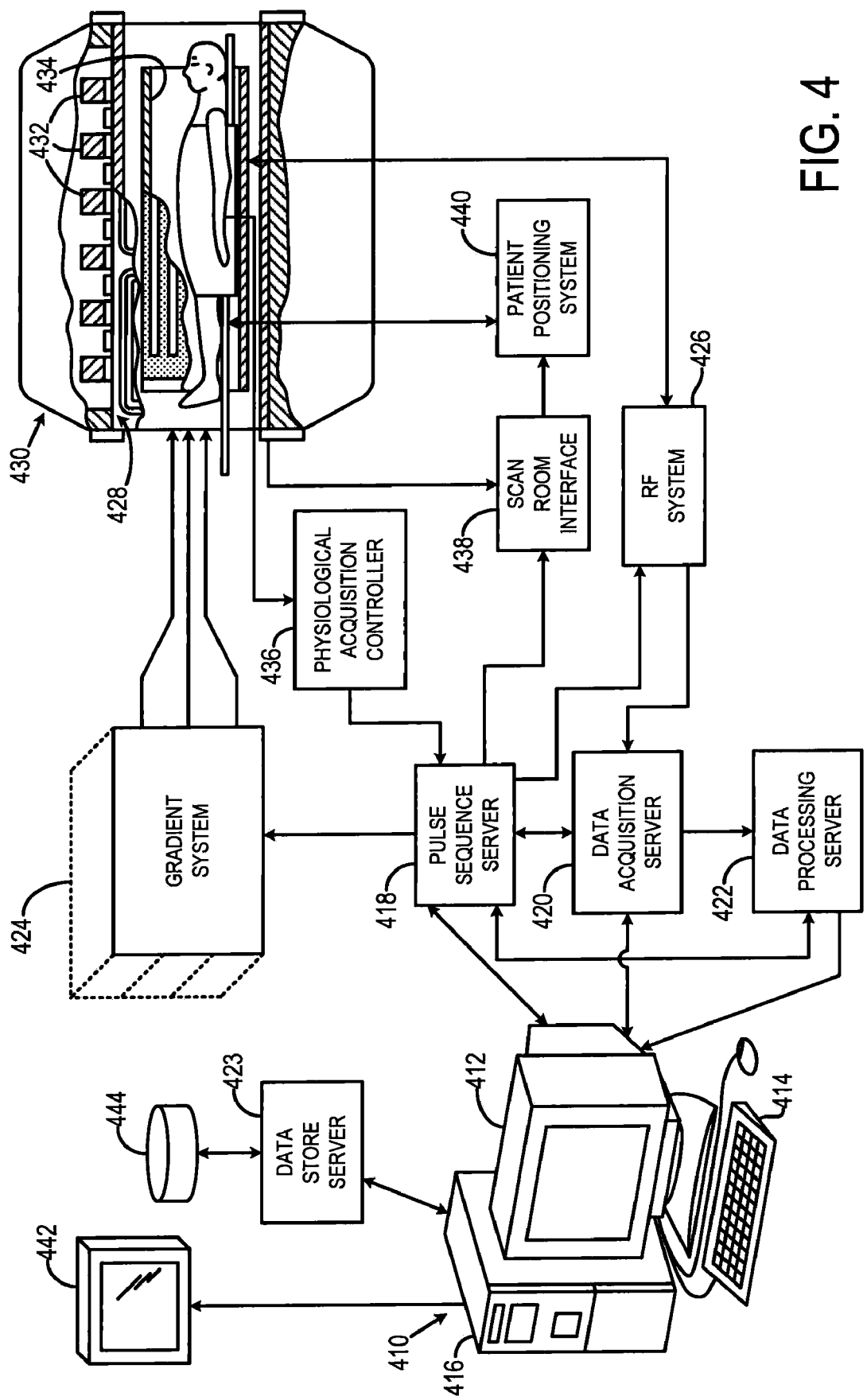
FIG. 4 is a block diagram of a magnetic resonance imaging (MRI) system, which employs an embodiment of the present invention.

Referring particularly to FIG. 4, the preferred embodiment of the invention is employed in an MRI system. The MRI system includes a workstation 410 having a display 412 and a keyboard 414. The workstation 410 includes a processor 416 that is a commercially available programmable machine running a commercially available operating system. The workstation 410 provides the operator interface that enables scan prescriptions to be entered into the MRI system. The workstation 410 is coupled to four servers: a pulse sequence server 418; a data acquisition server 420; a data processing server 422, and a data store server 423. The workstation 410 and each server 418, 420, 422 and 423 are connected to communicate with each other.

The pulse sequence server 418 functions in response to instructions downloaded from the workstation 410 to operate a gradient system 424 and an RF system 426. Gradient waveforms necessary to perform the prescribed scan are produced and applied to the gradient system 424 that excites gradient coils in an assembly 428 to produce the magnetic field gradients $G_x$, $G_y$, and $G_z$ used for position encoding MR signals. The gradient coil assembly 428 forms part of a magnet assembly 430 that includes a polarizing magnet 432 and a whole-body RF coil 434.

RF excitation waveforms are applied to the RF coil 434 by the RF system 426 to perform the prescribed magnetic resonance pulse sequence. Responsive MR signals detected by the RF coil 434 or a separate local coil (not shown in FIG. 4) are received by the RF system 426, amplified, demodulated, filtered and digitized under direction of commands produced by the pulse sequence server 418. The RF system 426 includes an RF transmitter for producing a wide variety of RF pulses used in MR pulse sequences. The RF transmitter is responsive to the scan prescription and direction from the pulse sequence server 418 to produce RF pulses of the desired frequency, phase and pulse amplitude waveform. The generated RF pulses may be applied to the whole body RF coil 434 or to one or more local coils or coil arrays (not shown in FIG. 4).

The RF system 426 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2},$$

and the phase of the received MR signal may also be determined:

$$\phi = \tan^{-1}\left(\frac{Q}{I}\right).$$

The pulse sequence server 418 also optionally receives patient data from a physiological acquisition controller 436. The controller 436 receives signals from a number of different sensors connected to the patient, such as ECG signals from electrodes or respiratory signals from a bellows. Such signals are typically used by the pulse sequence server 418 to synchronize, or "gate", the performance of the scan with the subject's respiration or heart beat.

The pulse sequence server 418 also connects to a scan room interface circuit 438 that receives signals from various sensors associated with the condition of the patient and the magnet system. It is also through the scan room interface circuit 438 that a patient positioning system 440 receives commands to move the patient to desired positions during the scan.

The digitized MR signal samples produced by the RF system 426 are received by the data acquisition server 420. The data acquisition server 420 operates in response to instructions downloaded from the workstation 410 to receive the real-time MR data and provide buffer storage such that no data is lost by data overrun. In some scans the data acquisition server 420 does little more than pass the acquired MR data to the data processor server 422. However, in scans that require information derived from acquired MR data to control the further performance of the scan, the data acquisition server 420 is programmed to produce such information and convey it to the pulse sequence server 418. For example, during prescans MR data is acquired and used to calibrate the pulse sequence performed by the pulse sequence server 418. Also, navigator signals may be acquired during a scan and used to adjust RF or gradient system operating parameters or to control the view order in which k-space is sampled. And, the data acquisition server 420 may be employed to process MR signals used to detect the arrival of contrast agent in a magnetic resonance angiography (MRA) scan. In all these examples the data acquisition server 420 acquires MR data and processes it in real-time to produce information that is used to control the scan.

The data processing server 422 receives MR data from the data acquisition server 420 and processes it in accordance with instructions downloaded from the workstation 410. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 422 are conveyed back to the workstation 410 where they are stored. Real-time images are stored in a data base memory cache (not shown) from which they may be output to operator display 412 or a display 442 that is located near the magnet assembly 430 for use by attending physicians. Batch mode images or selected real time images are stored in a host database on disc storage 444. When such images have been reconstructed and transferred to storage, the data processing server 422 notifies the data store server 423 on the workstation 410. The workstation 410 may be used by an operator to archive the images, produce films, or send the images via a network to other facilities.

Exemplary Pulse Sequence

Figure 5:
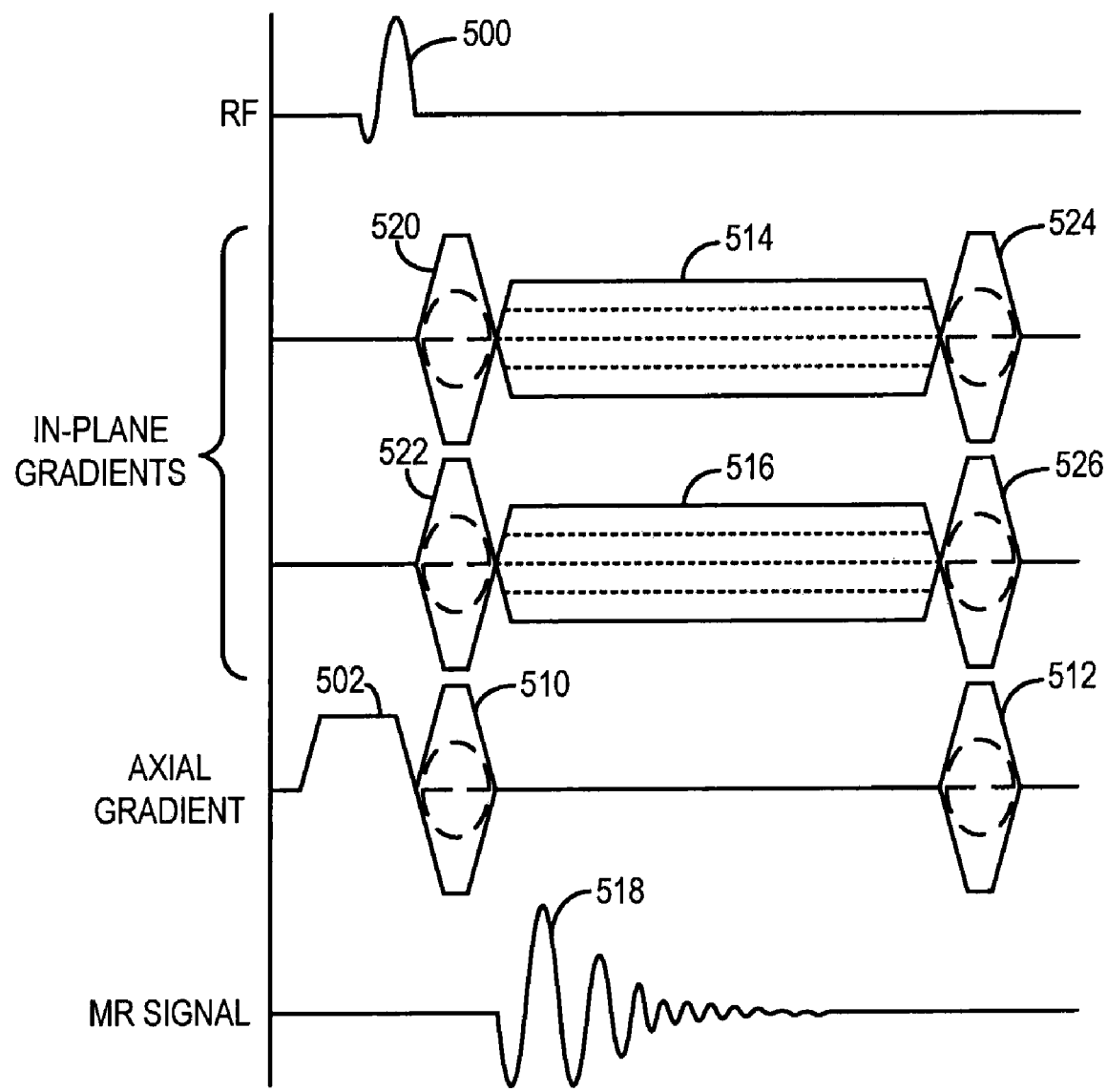
FIG. 5 is a graphic representation of a pulse sequence used in the MRI system of FIG. 4 to practice one embodiment of the present invention.
Figure 6:
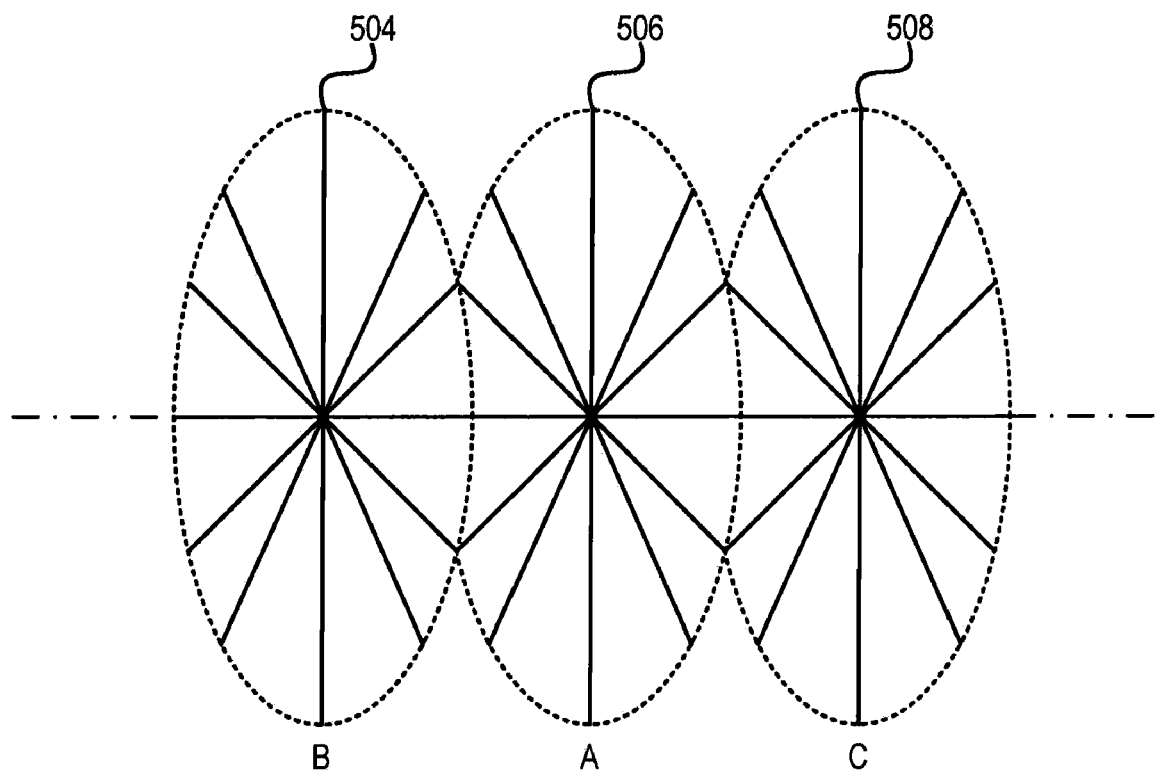
FIG. 6 is a pictorial representation of the k-space data sampled using the pulse sequence of FIG. 5.

When practicing an embodiment of the invention that employs the aforementioned MRI system, nuclear magnetic resonance (NMR) data is acquired using a projection reconstruction, or radial, pulse sequence, such as the one shown in FIG. 5. This is a fast gradient-recalled echo pulse sequence in which a selective, asymmetrically truncated sinc RF excitation pulse 500 is produced in the presence of a slice-select gradient 502. This pulse sequence may be used to acquire a single 2D slice by sampling in a single k-space circular plane, or it may be used to sample a plurality of circular k-space planes as shown at 504, 506 and 508 in FIG. 6. When multiple 2D slices are acquired the gradient 502 is a slab select gradient followed by a phase encoding gradient lobe 510 and a rewinder gradient lobe 512 of opposite polarity. This axial, phase encoding gradient 510 is stepped through values during the scan to sample from each of the 2D k-space planes 504, 506 and 508.

Two in-plane readout gradients 514 and 516 are played out during the acquisition of an NMR echo signal 518 to sample k-space in a 2D plane 504, 506, or 508 along a radial trajectory. These in-plane gradients, 514 and 516, are perpendicular to the axial gradient and they are perpendicular to each other. During a scan they are stepped through a series of values to rotate the view angle of the radial sampling trajectory as will be described in more detail below. Each of the in-plane readout gradients is preceded by a prephasing gradient lobe, 520 and 522, and followed by a rewinder gradient lobe, 524 and 526.

It should be apparent to those skilled in the art that sampling trajectories other than the preferred straight line trajectory extending from one point on the k-space peripheral boundary, through the center of k-space to an opposite point on the k-space peripheral boundary may also be used. One variation is to acquire a partial NMR echo signal 518 which samples along a trajectory that does not extend across the entire extent of the sampled k-space volume. An exemplary pulse sequence for this method can be found, for example, in U.S. Pat. No. 7,148,685. Another variation which is equivalent to the straight line projection reconstruction pulse sequence is to sample along a curved path, or spiral, rather than a straight line. Such pulse sequences are described, for example, by F. E. Boada, et al., in "Fast Three Dimensional Sodium Imaging," *Magnetic Resonance in Medicine*, 1997; 37:706-715, by K. V. Koladia, et al., in "Rapid 3D PC-MRA Using Spiral Projection Imaging", *Proc. Intl. Soc. Magn. Reson. Med.* 13, 2005, and by J. G. Pipe and K. V. Koladia in "Spiral Projection Imaging: a new fast 3D trajectory", *Proc. Intl. Soc. Mag. Reson. Med.* 13, 2005. It should further be appreciated by those skilled in the art that Cartesian sampling patterns can also be interleaved and employed to practice the present invention. Moreover, the present invention may be employed with 3D as well as 2D versions of these sampling methods and use of the term "pixel" herein is intended to refer to a location in either a 2D or a 3D image.

The MRI system described above can be used in a wide variety of clinical applications to acquire either 2D or 3D sets of projection views that may be used to reconstruct one or more images. The image reconstruction method of the present invention is particularly useful in scans where one or more image frames are reconstructed using less than all the acquired projection views. The present invention can further be practiced with parallel MR imaging techniques, as will be described in better detail below.

Image Reconstruction in an MR Imaging System

Figure 7:
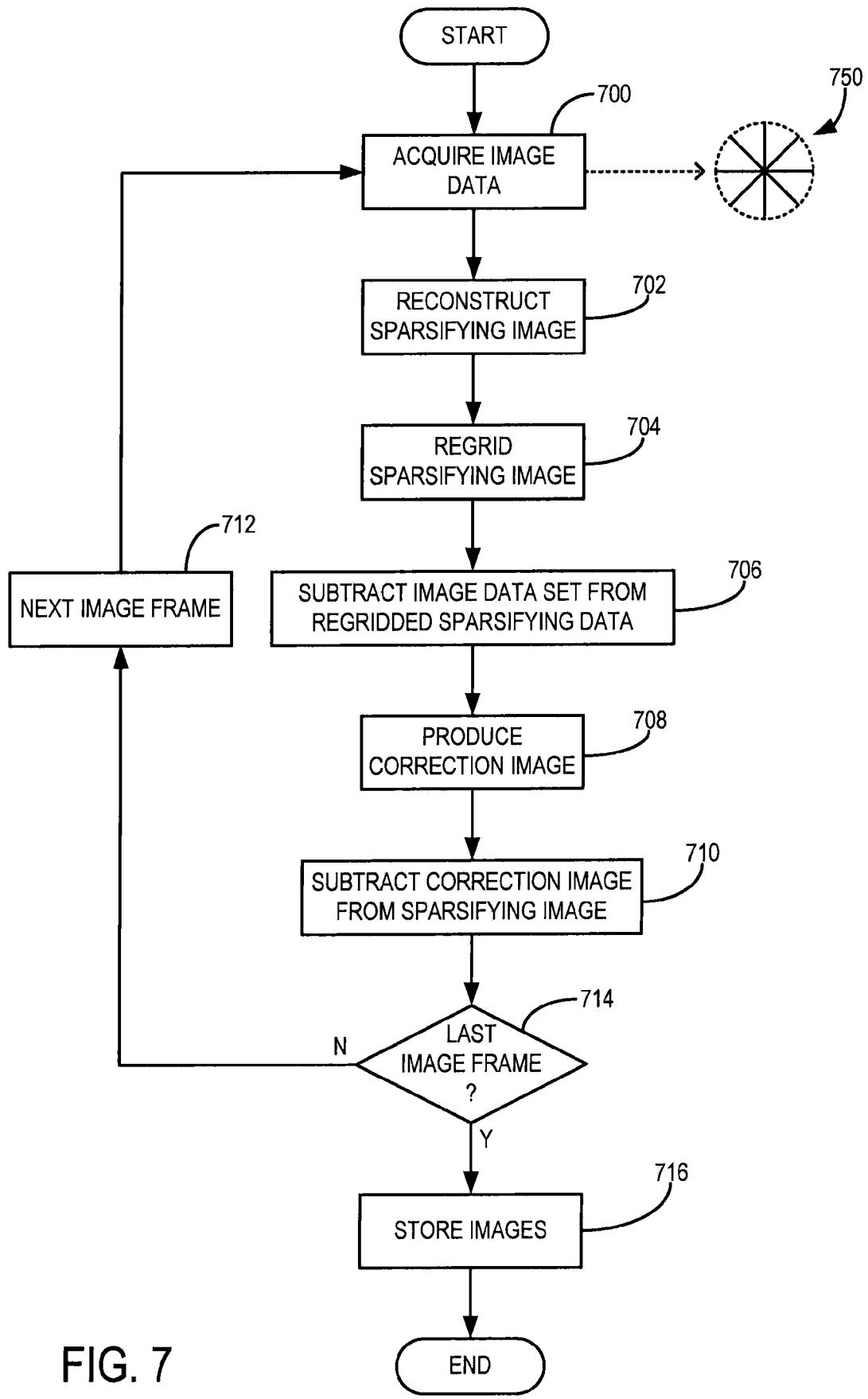
FIG. 7 is a flowchart of an embodiment of the invention used in the MRI system of FIG. 4 with the pulse sequence of FIG. 5.

The first embodiment of the image reconstruction method in accordance with the present invention employs an MRI system that acquires two-dimensional projection views and reconstructs a series of image frames that depict the subject over a period of time. Referring particularly to FIG. 7, a set of projection views 750 are acquired from which an image frame is to be reconstructed as indicated at process block 700. These projection views 750 are few in number (e.g., 10 views) and evenly distributed to sample k-space as uniformly as possible. Because of the low number of projection views that are acquired, this image frame can be acquired in a very short scan time, but because k-space is highly undersampled, streak artifacts will occur in any image reconstructed using conventional methods. The use of the term image data set herein is intended to refer to a set of projection views 750 acquired with a preselected number of repetitions of the pulse sequence described above with reference to FIG. 5.

Figure 8:
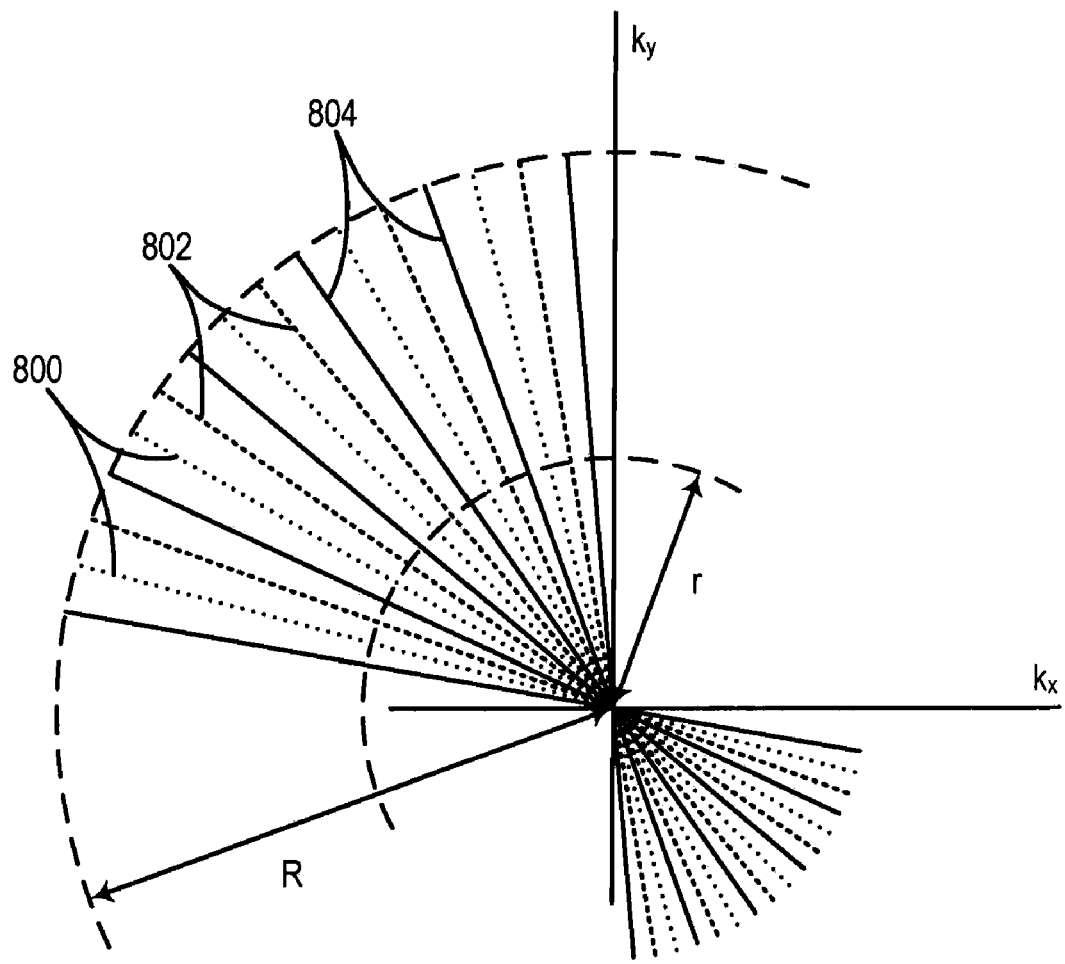
FIG. 8 is a graphic representation of interleaved projection views.

The next step as indicated at process block 702 is to combine all of the projection views that have been acquired from the subject of the examination and reconstruct a composite, or sparsifying, image, $I_s$. This will include projection views previously acquired which are interleaved with the views for the current image frame and which thus provides a more complete sampling of k-space. Referring to FIG. 8, for example, the current image frame projection views may sample k-space as indicated by dotted lines 800 and previously acquired image frame views may sample k-space as indicated by dashed lines 802 and lines 804. The sparsifying image may be reconstructed using a conventional method because a sufficient number of views are available to avoid image artifacts. In the preferred embodiment this reconstruction includes regridding the combined acquired k-space projection data into Cartesian coordinates and then performing an inverse two-dimensional Fourier transformation (2DFT) to produce the sparsifying image, $I_s$.

The current image frame is next reconstructed according to the teachings of the present invention. More specifically, the sparsifying image, $I_s$, is regridded into k-space along the same sampling pattern as the current image frame, as indicated in step 704. An exemplary regridding process is described by K. P. Pruessman, et al., in "Advances in Sensitivity Encoding With Arbitrary k-Space Trajectories," *Magnetic Resonance in Medicine,* 2001; 46:638-651. The current image data set is then subtracted from the regridded sparsifying image in step 706 to produce a difference data set. Since the sparsifying image has been regridded in the manner described above, it is no longer an interleaved set of k-space projection views as shown in FIG. 8; instead, the regridded data is a set of values in k-space having the same sampling pattern as the current image data set, but including information corresponding to a plurality of image frames. Therefore, when the subtraction occurs, the information contained in the current image data set is not simply removed from the regridded data as would be the case were the current image data set to be subtracted from the sliding window composite of the image frames acquired in step 700.

A correction image is produced next in step 708. First, the k-space projection views in the difference data set are transformed to x-ray projection, or sinogram, space by performing a one-dimensional, fast Fourier inverse transformation to produce the vector $Y_{corr}$. This is repeated for each projection view in the difference data set to form a matrix of difference data vectors, $Y_{corr}$. The encoding matrix, A, is then selected to be a Radon transform matrix. In the alternative, the matrix of difference data vectors, $Y_{corr}$, can contain k-space values and the corresponding encoding matrix, A, can be selected as a Fourier transform matrix. A fixed value of the control parameter, $\lambda$, and an appropriate sparsifying transform $\Psi$ are selected and the minimization problem presented in equation (19) is iteratively solved to produce the correction image for the current image frame. The minimization problem is solved using an iteratively reweighed algorithm such as the one described by I. F. Gorodnitsky and B. D. Rao in "Sparse Signal Reconstruction from Limited Data Using FOCUSS: A Re-weighted Minimum Norm Algorithm" *IEEE Transactions on Signal Processing,* 1997; 45(3):600-616. In the alternative, non-iterative image reconstruction methods as well as other iterative reconstruction methods may be employed, such as, for example, the one described by B. Wohlberg and P. Rodriguez in "An Iteratively Reweighted Norm Algorithm for Minimization of Total Variation Functionals" *IEEE Signal Processing Letters,* 2007; 14(12):948-951. The sparsifying transform, $\Psi$, is selected to be an image gradient D, where D is a matrix of first order image differences. In the alternative, however, $\Psi$ can be selected to be a discrete wavelet transform or an identity matrix. The choice of $\Psi$ can vary and it should be appreciated by those skilled in the art that many variations are possible and are all within the scope of the present invention.

The correction image, $I_{corr}$, has pixel values indicative of image intensity differences between the sparsifying image and the underlying current image frame. As such, the final image corresponding to the current image frame is then produced in step 710 where the correction image is subtracted from the sparsifying image, $I_{corr}$. The a priori information embodied in the sparsifying image is used to constrain and thereby improve the quality of the reconstructed image frames.

Additional image frames are reconstructed as indicated at process block 712. When the last image frame is completed as determined at decision block 714, the reconstruction process stops and all the image frames are stored as indicated at process block 716.

Parallel Image Reconstruction in an MR Imaging System

Figure 9:
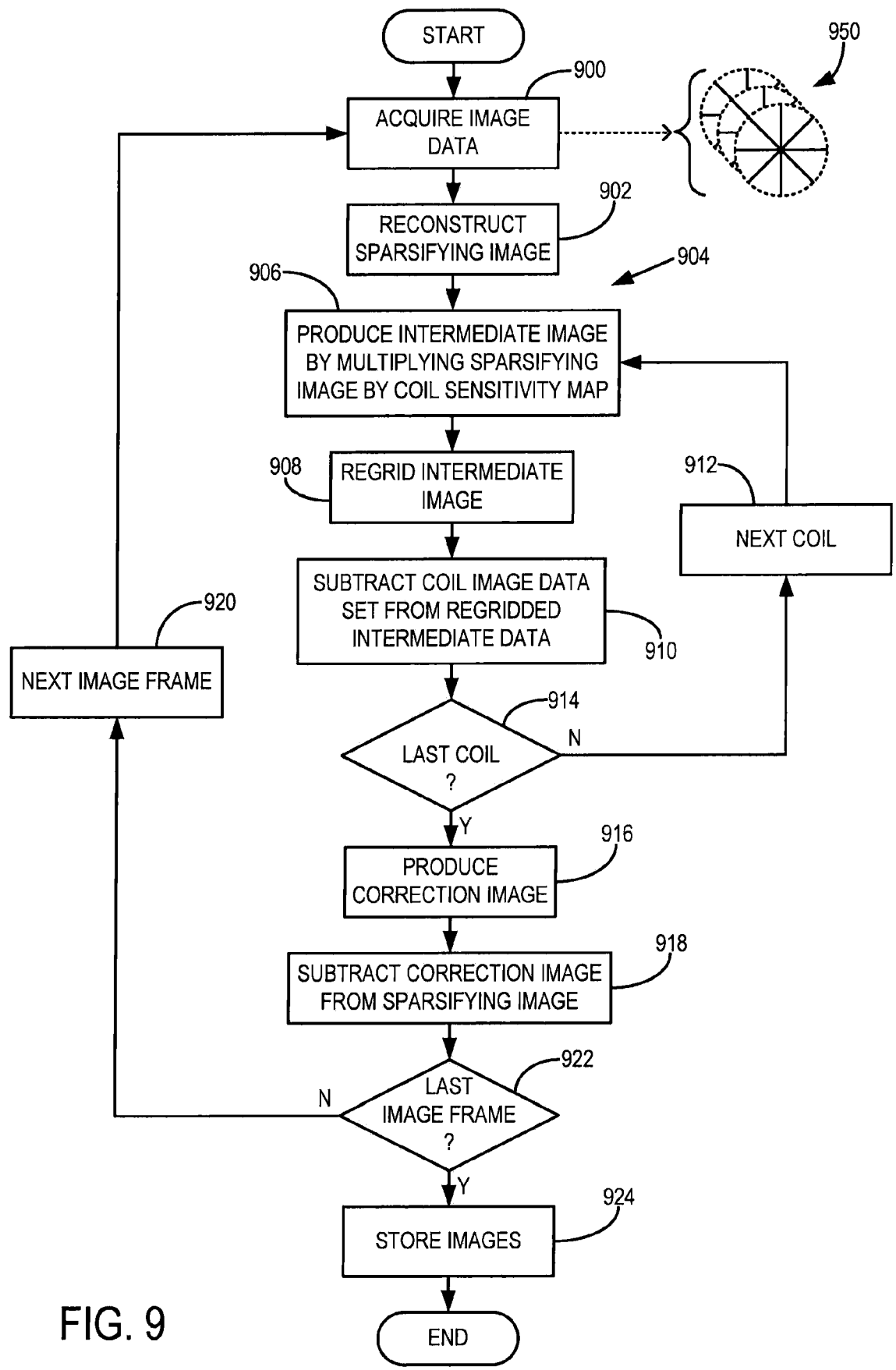
FIG. 9 is a flowchart of another embodiment of the invention used in the MRI system of FIG. 4 with the pulse sequence of FIG. 5.

Another embodiment of the image reconstruction method also employs an MRI system that acquires two-dimensional projection views and reconstructs a series of image frames that depict the subject over a period of time. In this embodiment, however, the image data is acquired using a parallel RF receive coil array and one image data set is acquired from each receive coil element, collectively forming a "coil image data set" 950. Referring particularly to FIG. 9, a coil image data set is acquired from which an image frame is to be reconstructed as indicated at process block 900. The projection views making up each image data set within the coil image data set 950 are few in number and evenly distributed to sample k-space as uniformly as possible. Because of the low number of projection views that are acquired, each image frame can be acquired in a very short scan time, but because k-space is highly undersampled, streak artifacts will occur in any image reconstructed using conventional methods. By employing a parallel MR acquisition scheme, an even further reduction of overall scan time is achievable.

The next step as indicated at process block 902 is to combine all of the projection views that have been acquired from the subject of the examination and reconstruct a composite, or sparsifying, image, $I_s$. First, the image data sets for each coil element in the parallel receiver array are combined. Each of these combined image data sets will include projection views previously acquired which are interleaved with the views for the current image frame and which thus provides a more complete sampling of k-space. Referring to FIG. 8, for example, the current image frame projection views may sample k-space as indicated by dotted lines 800 and previously acquired image frame views may sample k-space as indicated by dashed lines 802 and lines 804. However, k-space is still undersampled and parallel MR image reconstruction methods are employed to produce a sparsifying image, $I_s$, from the combined image data sets from each coil element. The sparsifying image may be reconstructed using a conventional parallel reconstruction method with the choice of reconstruction method depending on the k-space trajectory employed to practice the present invention. For example, a non-Cartesian SENSE method can be employed, such as the one described by K. P. Pruessman, et al., in "Advances in Sensitivity Encoding with Arbitrary k-Space Trajectories," *Magnetic Resonance in Medicine*, 2001; 46:638-651.

A loop is then entered at 904, in which a sparsified image data set is produced from the coil image data set 950. More specifically, for each coil element the sparsifying image, $I_s$, is first multiplied by the corresponding coil sensitivity map, as indicated in step 906 to produce an intermediate image. Each intermediate image is then regridded into k-space along the same sampling pattern as the current image frame in step 908. The current image data set for the corresponding coil element is then subtracted from the regridded intermediate image in step 910 to produce a difference data set for that coil. This process is repeated for the image data set corresponding to the next coil element, as indicated in step 912. When a difference data set has been produced for the current image frame for each coil in the parallel receiver array, as determined at decision block 914, the reconstruction process for the current image frame continues.

A correction image is produced next in step 916. First, the k-space projection views in the difference data set are transformed to x-ray projection, or sinogram, space by performing a one-dimensional, fast Fourier inverse transformation to produce the vector $Y_{corr}$, and an appropriate encoding matrix, A, is further produced. Additionally, each difference data vector, $Y_{corr}$, includes information for a given projection view from each coil in the parallel receiver coil array. As described above, the difference data vectors, $Y_{corr}$, can alternatively contain k-space values. A fixed value of the control parameter, $\lambda$, and an appropriate sparsifying transform $\Psi$ are selected and the minimization problem presented in equation (19) is iteratively solved to produce the correction image for the current image frame. In this embodiment, the encoding matrix, A, is selected to include the coil sensitivity profiles of each coil element in the parallel receiver array. The minimization problem is solved using an iteratively reweighed algorithm such as the one described by I. F. Gorodnitsky and B. D. Rao in "Sparse Signal Reconstruction from Limited Data Using FOCUSS: A Re-weighted Minimum Norm Algorithm" *IEEE Transactions on Signal Processing*, 1997; 45(3): 600-616. In the alternative, non-iterative image reconstruction methods as well as other iterative reconstruction methods may be employed, such as, for example, the one described by B. Wohlberg and P. Rodriguez in "An Iteratively Reweighted Norm Algorithm for Minimization of Total Variation Functionals" *IEEE Signal Processing Letters*, 2007; 14(12):948-951. The sparsifying transform, $\Psi$, is selected to be an image gradient D, where D is a matrix of first order image differences. In the alternative, $\Psi$ can be selected to be a discrete wavelet transform or an identity matrix. The choice of $\Psi$ can vary and it should be appreciated by those skilled in the art that many variations are possible and are all within the scope of the present invention.

The final image corresponding to the current image frame is then produced in step 916 where the correction image is subtracted from the sparsifying image, $I_s$. The a priori information embodied in the sparsifying image is used to constrain and thereby improve the quality of the reconstructed image frames. Additional image frames are reconstructed as indicated at process block 920. When the last image frame is completed as determined at decision block 922, the reconstruction process stops and all the image frames are stored as indicated at process block 924.

X-Ray Computed Tomography Imaging System

Figure 10A:
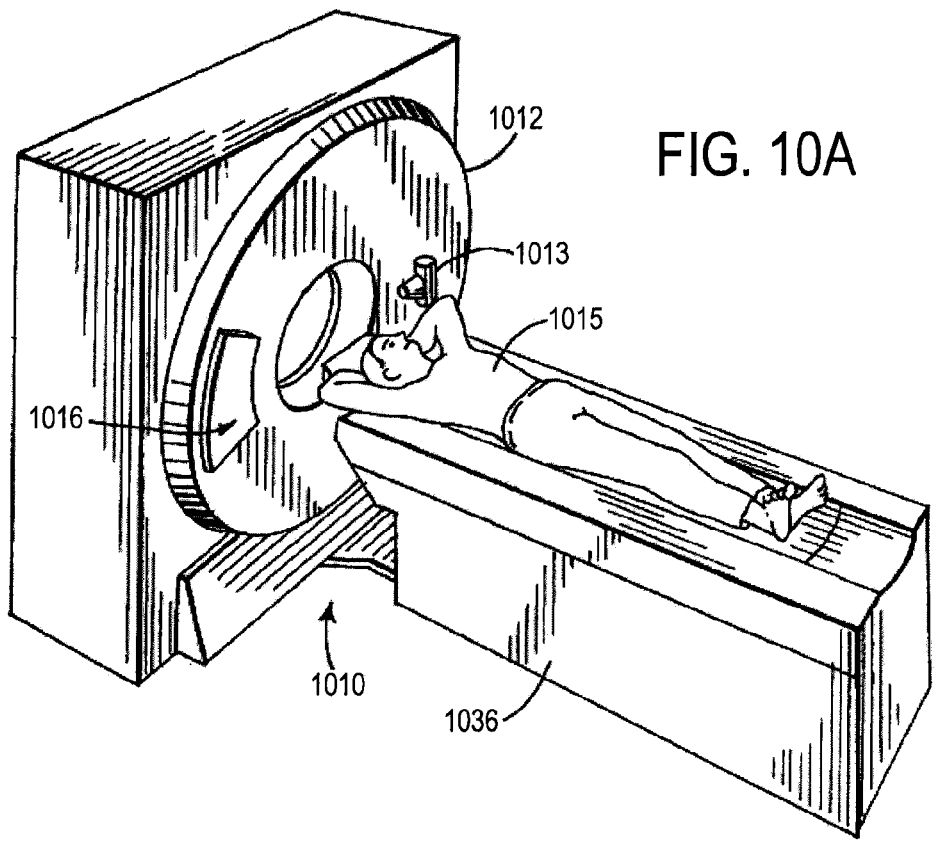
FIG. 10A is a pictorial view of an x-ray computed tomography (CT) imaging system, which employs another embodiment of the present invention.
Figure 10B:
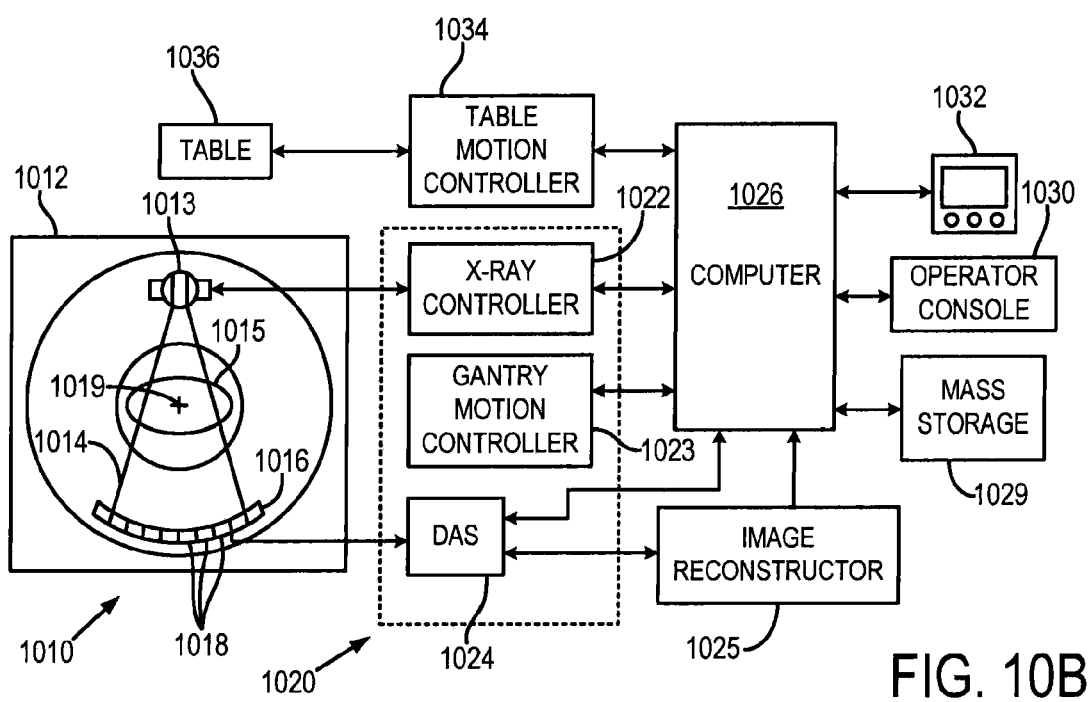
FIG. 10B a block diagram of the CT imaging system of FIG. 10B.

The present invention is also particularly applicable to other medical imaging modalities in which interleaved projection views of the subject are acquired. One such imaging modality is x-ray computed tomography. With initial reference to FIGS. 10A and 10B, an x-ray computed tomography (CT) imaging system 1010 includes a gantry 1012 representative of a "third generation" CT scanner. Gantry 1012 has an x-ray source 1013 that projects a fan-beam, or cone-beam, of x-rays 1014 toward a detector array 1016 on the opposite side of the gantry. The detector array 1016 is formed by a number of detector elements 1018 which together sense the projected x-rays that pass through a medical patient 1015. Each detector element 1018 produces an electrical signal that represents the intensity of an impinging x-ray beam and hence the attenuation of the beam as it passes through the patient. During a scan to acquire x-ray projection data, the gantry 1012 and the components mounted thereon rotate about a center of rotation 1019 located within the patient 1015.

The rotation of the gantry and the operation of the x-ray source 1013 are governed by a control mechanism 1020 of the CT system. The control mechanism 1020 includes an x-ray controller 1022 that provides power and timing signals to the x-ray source 1013 and a gantry motor controller 1023 that controls the rotational speed and position of the gantry 1012. A data acquisition system (DAS) 1024 in the control mechanism 1020 samples analog data from detector elements 1018 and converts the data to digital signals for subsequent processing. An image reconstructor 1025, receives sampled and digitized x-ray data from the DAS 1024 and performs high speed image reconstruction. The reconstructed image is applied as an input to a computer 1026 which stores the image in a mass storage device 1028.

The computer 1026 also receives commands and scanning parameters from an operator via console 1030 that has a keyboard. An associated display 1032 allows the operator to observe the reconstructed image and other data from the computer 1026. The operator supplied commands and parameters are used by the computer 1026 to provide control signals and information to the DAS 1024, the x-ray controller 1022 and the gantry motor controller 1023. In addition, computer 1026 operates a table motor controller 1034 which controls a motorized table 1036 to position the patient 1015 in the gantry 1012.

Like the MRI system, the CT system has many different clinical applications in which either 2D or 3D sets of projection views are acquired and used to reconstruct one or more images of the patient. Whereas the projection views acquired by the MRI system are comprised of k-space (or Fourier space) samples, the projection views acquired by the CT system are comprised of x-ray projection space samples. Image reconstruction using data acquired with a CT system necessarily requires transformation from x-ray projection space to real space.

Image Reconstruction in a CT Imaging System

Figure 11:
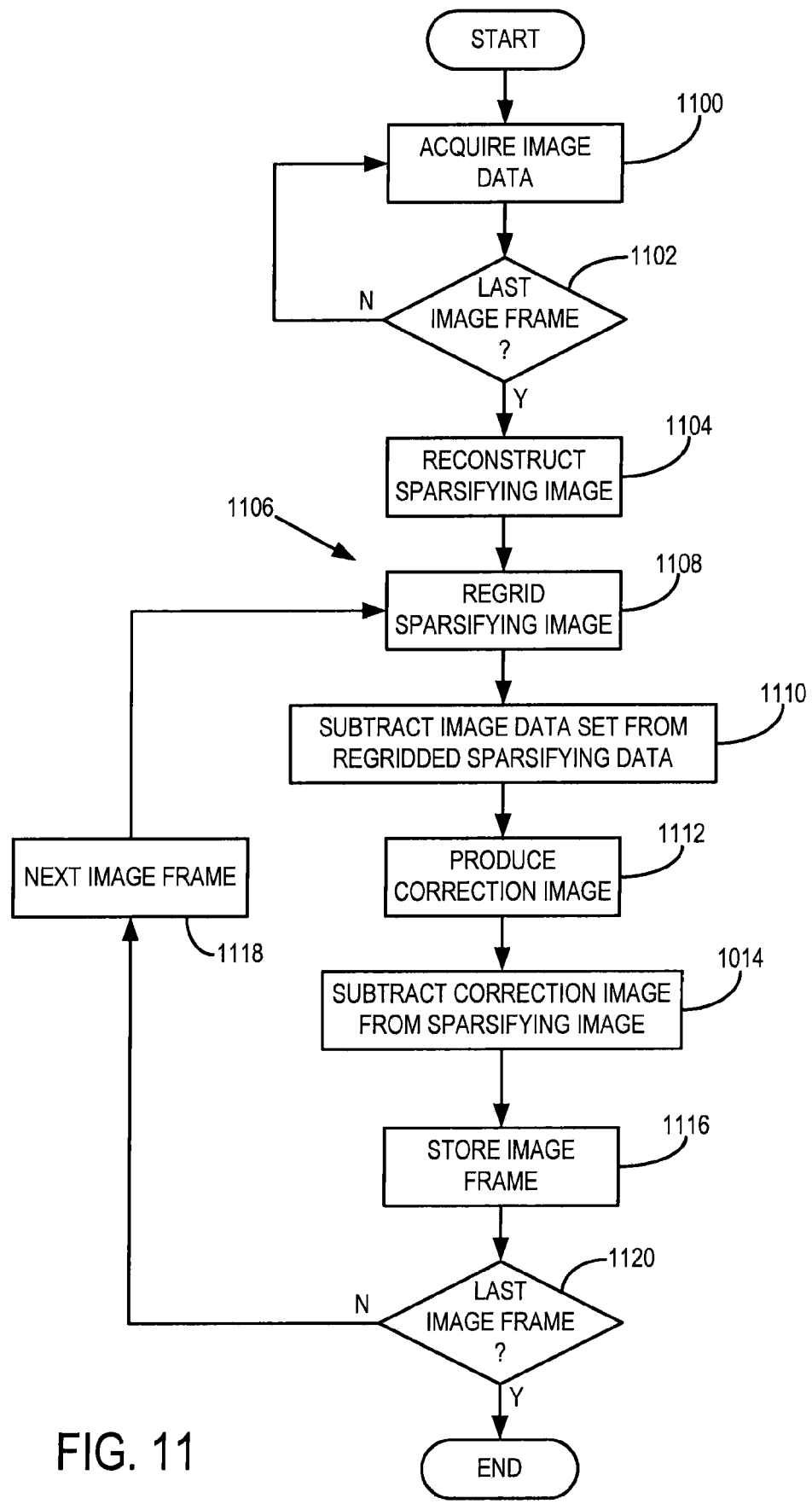
FIG. 11 is a flowchart of an embodiment of the invention used in the CT imaging system of FIGS. 10A and 10B.

Referring particularly to FIG. 11, another embodiment of the invention employs a CT system to acquire a series of 2D slice images. As indicated by process block 1100 a set of projection views from which a 2D image frame can be reconstructed is acquired. This may be a highly undersampled acquisition in which the projection views are at equally spaced view angles that sample x-ray projection space in a uniform manner. In this embodiment, the data acquisition phase of the scan is completed prior to image reconstruction and a series of image frames are thus acquired before this phase of the scan is completed as determined at decision block 1102. For example, a series of image frames may be acquired during a dynamic study in which a contrast agent flows into the region of interest. As with the first embodiment described above, the projection views acquired during this scan are interleaved as illustrated in FIG. 8 such that when they are all combined, a data set is formed in which x-ray projection space is highly sampled even though each image data set undersamples x-ray projection space.

As indicated at process block 1104, a sparsifying image is reconstructed from the combined projection views acquired during the acquisition phase of the scan. The sets of equally spaced projection views that form each image frame are interleaved with each other such that the projection views from a combination of image frames more fully sample x-ray projection space and produce a higher quality image. The sparsifying image is reconstructed from these combined projection views using a conventional image reconstruction technique such as a filtered backprojection.

A loop is entered into at 1106 where the reconstruction method described above may now be used to reconstruct each frame image. First, the sparsifying image is regridded to the same sampling pattern as the image frame that is to be reconstructed, as indicated in step 1108. Next, the current image data is subtracted from the regridded sparsified data to produce a difference data set in step 1110. The difference data set is then employed in the minimization problem presented in equation (19) above to produce a correction image in step 1112. Since the data acquired with a CT imaging system is inherently in x-ray projection space, the difference data need not be transformed before the iterative minimization process. In the alternative, non-iterative methods, such as, filtered backprojection methods can be employed to reconstruct the correction image. As described above, the encoding matrix in this situation is the Radon transform matrix and a control parameter, A, and an appropriate sparsifying transform, $\Psi$, are selected. The corrected image frame is then produced in step 1114 by subtracting the correction image from the sparsifying image. The resulting corrected image frame is stored as indicated at process block 1116.

Further image frames are reconstructed as indicated at process block 1018 until all the data acquired during the data acquisition phase of the scan is used as determined at decision block 1120. The reconstruction phase of the scan ends at this point, although the reconstructed image frames may be further processed depending on the particular clinical application. In this embodiment the sparsifying image is formed by all the views acquired during the scan to provide a substantial improvement in image frame SNR, but the image frames are not available in real time.

Positron Emission Tomography Imaging System

In the above-described embodiments the a priori information used to reconstruct the sparsifying image results from the acquisition of a plurality of image frames at interleaved projection views. There are other clinical applications of the present invention, however, in which a priori information is available for a quality sparsifying image without acquiring additional projection views. One of these is data acquired with a positron emission tomography (PET) scanner.

Figure 12:
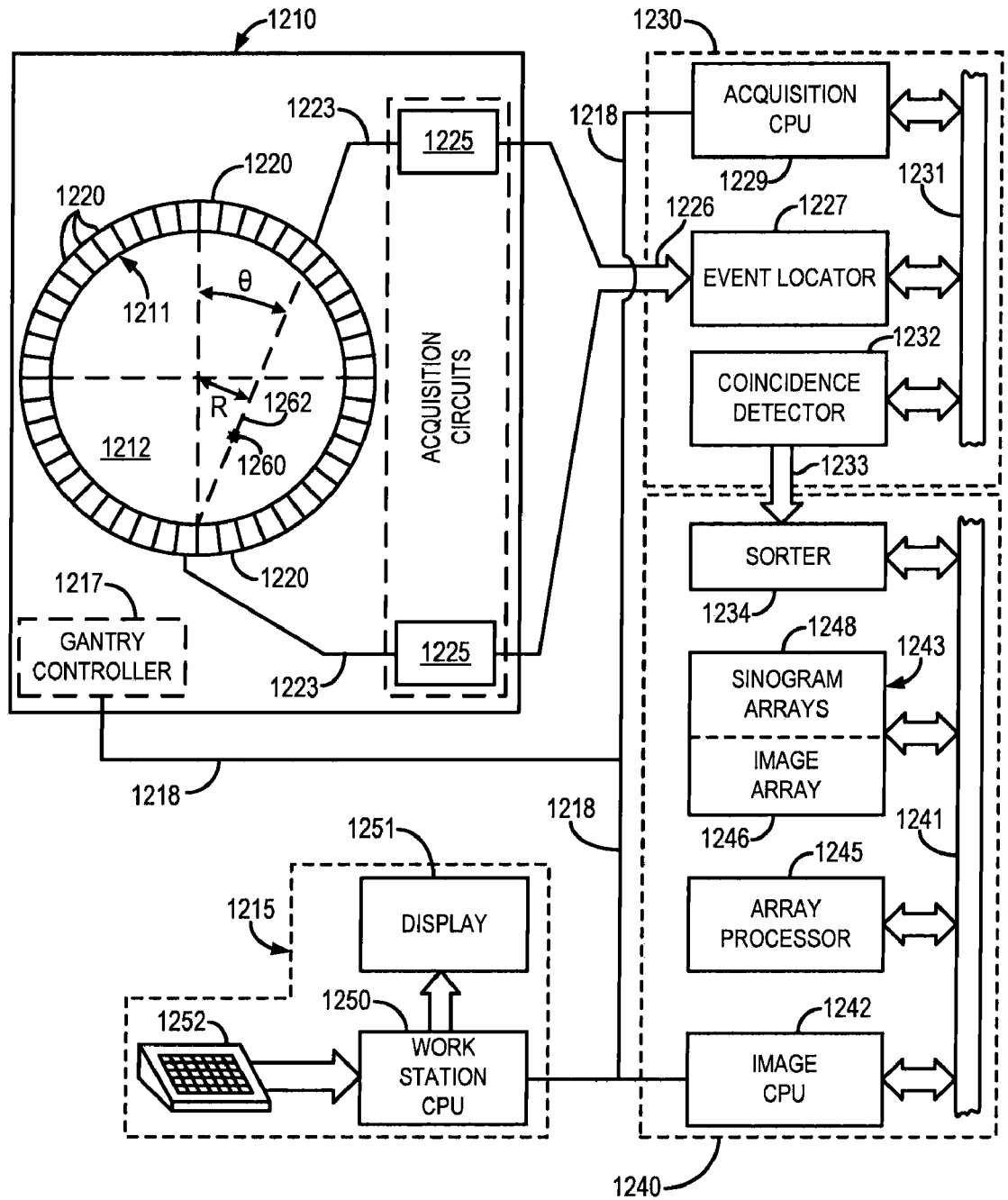
FIG. 12 is a block diagram of a positron emission tomography (PET) imaging system, which employs yet another embodiment of the present invention.

Referring particularly to FIG. 12, the PET scanner system includes a gantry 1210 which supports a detector ring assembly 1211 about a central opening, or bore 1212. A gantry controller 1217 is mounted within the gantry 1210 and is responsive to commands received from an operator work station 1215 through a second serial communication link 1218 to operate the gantry.

The detector ring 1211 is comprised of detector blocks 1220. Each block 1220 includes a set of scintillator crystal photomultiplier tubes. A set of acquisition circuits 1225 are mounted within the gantry 1210 to receive the signals from each of the modules 1220 in the detector ring 1211. The acquisition circuits 1225 determine the event coordinates within each block of scintillator crystals and these coordinates (x,z), along with the sum of the crystal block signals are digitized and sent through a cable 1226 to an event locater circuit 1227 housed in a separate cabinet 1228. Each acquisition circuit 1225 also produces an event detection pulse (EDP) which indicates the exact moment the scintillation event took place.

The event locator circuits 1227 form part of a data acquisition processor 1230 which periodically samples the signals produced by the acquisition circuits 1225. The processor 1230 has a backplane bus structure 1231 and an acquisition CPU 1229 which controls communications on this bus 1231 and links the processor 1230 to the local area network 1218. The event locator 1227 is comprised of a set of separate circuit boards which each connect to the cable 1226 and receive signals from corresponding acquisition circuits 1225 in the gantry 1210. The event locator 1227 synchronizes the event with the operation of the processor 1230 by detecting the event pulse (EDP) produced by an acquisition circuit 1225, and converting it into an 8-bit time marker which indicates when within the current sample period the scintillation event took place. Also, this circuit 1227 discards any detected events if the total energy of the scintillation is outside the range of 511 keV±20 percent. During each sample period, the information regarding each valid event is assembled into a set of digital numbers that indicate precisely when the event took place and the position of the scintillator crystal which detected the event. This event data packet is conveyed to a coincidence detector 1232 which is also part of the data acquisition processor 1230.

The coincidence detector 1232 accepts the event data packets from the event locators 1227 and determines if any two of them are in coincidence. Events which cannot be paired are discarded, but coincident event pairs are located and recorded as a coincidence data packet that is conveyed through a serial link 1233 to a sorter 1234. Each coincidence data packet includes a pair of digital numbers which precisely identify the addresses of the two scintillator crystals that detected the event. From these, the location and angle of the ray path that produced the coincidence event can be determined.

The sorter 1234 is a circuit which forms part of an image reconstruction processor 1240. The image reconstruction processor 1240 is formed about a backplane bus 1241. An image CPU 1242 controls the backplane bus 1241 and it links the processor 1240 to the local area network 1218. A memory module 1243 also connects to the backplane 1241 and it stores the data used to reconstruct images as will be described in more detail below. An array processor 1245 also connects to the backplane 1241 and it operates under the direction of the image CPU 1242 to perform the image reconstruction using the data in memory module 1243. The resulting image array 1246 is stored in memory module 1243 and is output by the image CPU 1242 to the operator work station 1215.

The function of the sorter 1234 is to receive the coincidence data packets and generate from them memory addresses for the efficient storage of the coincidence data. The set of all coincidence event rays that point in the same direction, $\theta$, and pass through the scanner's field of view is a complete projection, or "view". The distance, R, between a particular ray path in a projection view and the center of the field of view locates that ray within the view. As shown in FIG. 12, for example, an event 1260 occurs along a projection ray 1262 which is located in a view at the projection angle, $\theta$, and the distance, R. The sorter 1234 counts all of the events that occur on this projection ray (R,$\theta$) during the scan by sorting out the coincidence data packets that indicate an event at the two scintillator crystals lying on this projection ray. During an emission scan, the coincidence counts are organized in memory 1243 as a set of two-dimensional arrays, one for each axial image, and each having as one of its dimensions the projection angle, $\theta$, and the other dimension the distance, R. This $\theta$-by-R map of the measured coincidence events is called a histogram, or more commonly the sinogram array 1248.

Coincidence events occur at random and the sorter 1234 quickly determines the $\theta$ and R values from the two scintillator crystal addresses in each coincidence data packet and increments the count of the corresponding sinogram array element. At the completion of the emission scan, the sinogram array 1248 stores the total number of annihilation events which occurred along each ray. The number of such annihilation events indicates the number of positron electron annihilation events that occurred along the ray (R,$\theta$) during the emission scan and within a few minutes hundreds of thousands of events are typically recorded. These numbers are used to reconstruct a tomographic image.

It can be appreciated that the quality of a PET image will depend to a great extent on the number of scintillation events that are allowed to accumulate in the sinogram 1248. The longer the scan continues, the larger the number of detected scintillation events and the higher the quality of the reconstructed image.

Image Reconstruction in a PET Imaging System

Figure 13:
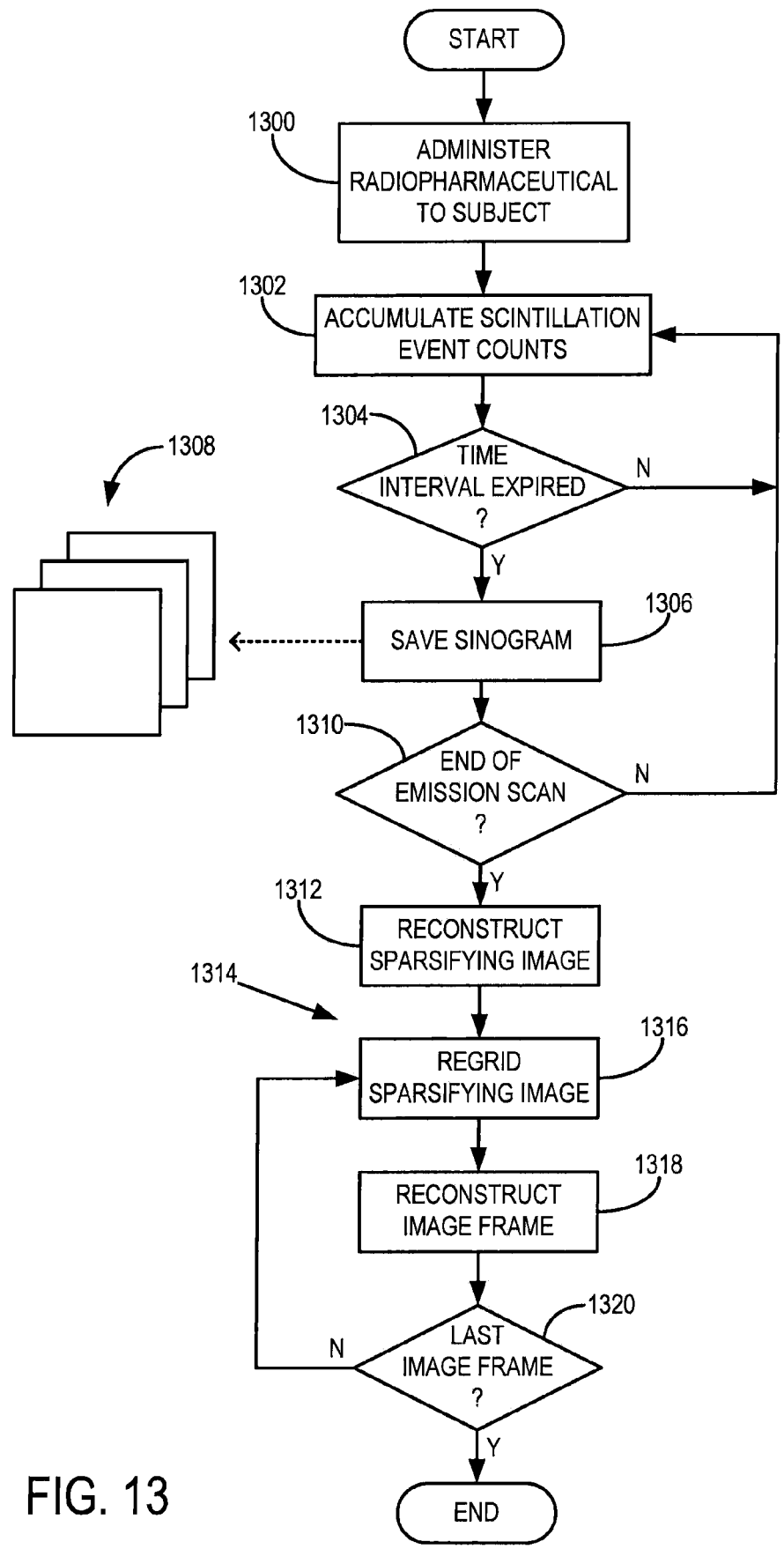
FIG. 13 is a flowchart of yet another embodiment of the invention using the PET imaging system of FIG. 12.

Referring particularly to FIG. 13, the present invention may be employed by the PET scanner to perform a time-resolved emission scan. The emission scan begins as indicated at process block 1300 by injecting a radionuclide into the subject of the examination. The radionuclides most often employed in diagnostic imaging are fluorine-18 ($^{18}$F), carbon-11 ($^{11}$C), nitrogen-13 ($^{13}$N), and oxygen-15 ($^{15}$O). These are employed as radioactive tracers called "radiopharmaceuticals" by incorporating them into substances, such as glucose or carbon dioxide. The radiopharmaceuticals are injected in the patient and become involved in such processes as glucose metabolism, fatty acid metabolism and protein synthesis.

The subject is placed in the bore 1212 of the PET scanner and scintillation events are detected and counted as indicated at process block 1302. As described above, the scintillation events are detected, sorted and stored in sinogram 1248 as counts for each ray R in the projection views $\theta$. Events are counted and accumulated for a relatively short time interval as determined at decision block 1304. This time interval determines the time resolution of the emission scan and it may be, for example, one-tenth the duration of a conventional emission scan. As indicated at process block 1306, when the time interval expires the accumulated scintillation event counts are saved as a time interval sinogram 1308.

The emission scan continues and the accumulated sinogram count is saved after each time interval until the end of the scan is detected at decision block 1310. End of scan may be a preset time or a preset number of time intervals. In either case, a plurality of time interval sinograms 1308 will be produced during the emission scan and the last sinogram 1308 will store the total count for the entire emission scan. Each time interval sinogram 1308 is analogous to an image data set acquired with the MR and CT imaging systems described above.

The image reconstruction phase of the scan now begins, and during this phase an image frame indicative of the uptake of radiopharmaceutical at the end of each time interval is reconstructed. First, as indicated at process block 1312, a sparsifying image is reconstructed. This is a conventional backprojection reconstruction using the last sinogram 1308 saved during the emission scan. This contains the accumulated scintillation events for the entire emission scan and the image quality will be the best possible.

A loop is then entered at 1314 in which time resolved image frames are reconstructed using this sparsifying image. More specifically, as indicated at process block 1316 an iterative reconstruction of each stored time interval sinogram 1308 is performed. This iterative reconstruction is performed as described above in equation (19) by first regridding the recently reconstructed sparsifying image, as indicated in step 1316 and described above. This is a constrained minimization problem in which the accumulated scintillation count for each ray, R, in each view, $\theta$, of the time interval sinogram 1308 is entered as the data vector s into equation (19). Additionally, and as described with reference to the other embodiments of the present invention, a difference data set is produced for each time interval sinogram 1308 by subtracting said time interval sinogram 1308 from the regridded sparsifying image data.

The image frame reconstruction process 1318 is repeated until image frames corresponding to each time interval sinogram 1308 is produced as detected at decision block 1320. As a result, a series of image frames are produced which indicate the uptake of the radiopharmaceutical at each time interval during the emission scan. By using the higher quality sparsifying image in the reconstruction, the image quality of each image frame is substantially improved over conventional images reconstructed using sinograms having low annihilation event counts.

In this PET scanner embodiment the sparsifying image is not formed using additional interleaved views acquired during the scan, but rather, by combining the data acquired at the same set of views during each of a plurality of time intervals during the scan. Sparsifying image quality is improved in this embodiment by increasing the SNR of each view rather than increasing the number of views as in the prior embodiments described above. This same strategy can also be used in x-ray CT, for example, to reduce patient x-ray exposure without reducing image quality. In such an embodiment a series of image frames are acquired using the same set of projection angles in each image frame. However, the x-ray dose is lowered to reduce the exposure for the patient. The frame image SNR is retained by using the reconstruction method of the present invention with a sparsifying image produced by combining the low-dose attenuation measurements made during each image frame acquisition. Rather than adding coincidence event counts as in the PET scanner embodiment, the "combination" in this x-ray embodiment is the average of all the corresponding attenuation measurements in acquired frame images.

This same image reconstruction strategy can be used in reconstructing images acquired with single photon emission computed tomography (SPECT) systems. As with PET scanners, SPECT systems accumulate counts of detected photons emitted from the subject along different ray paths. During a scan a gamma camera is moved slowly to accumulate counts at different view angles. Using the present invention a series of image frames may be acquired by moving the gamma camera more quickly and repeatedly through the same series of view angles. A lower count is accumulated at each view angle so as not to increase total scan time, but the SNR of each reconstructed image frame is maintained using a sparsifying image that is formed by adding all the counts together for each view angle.

Image-Guided Radiation Therapy System

Figure 14:
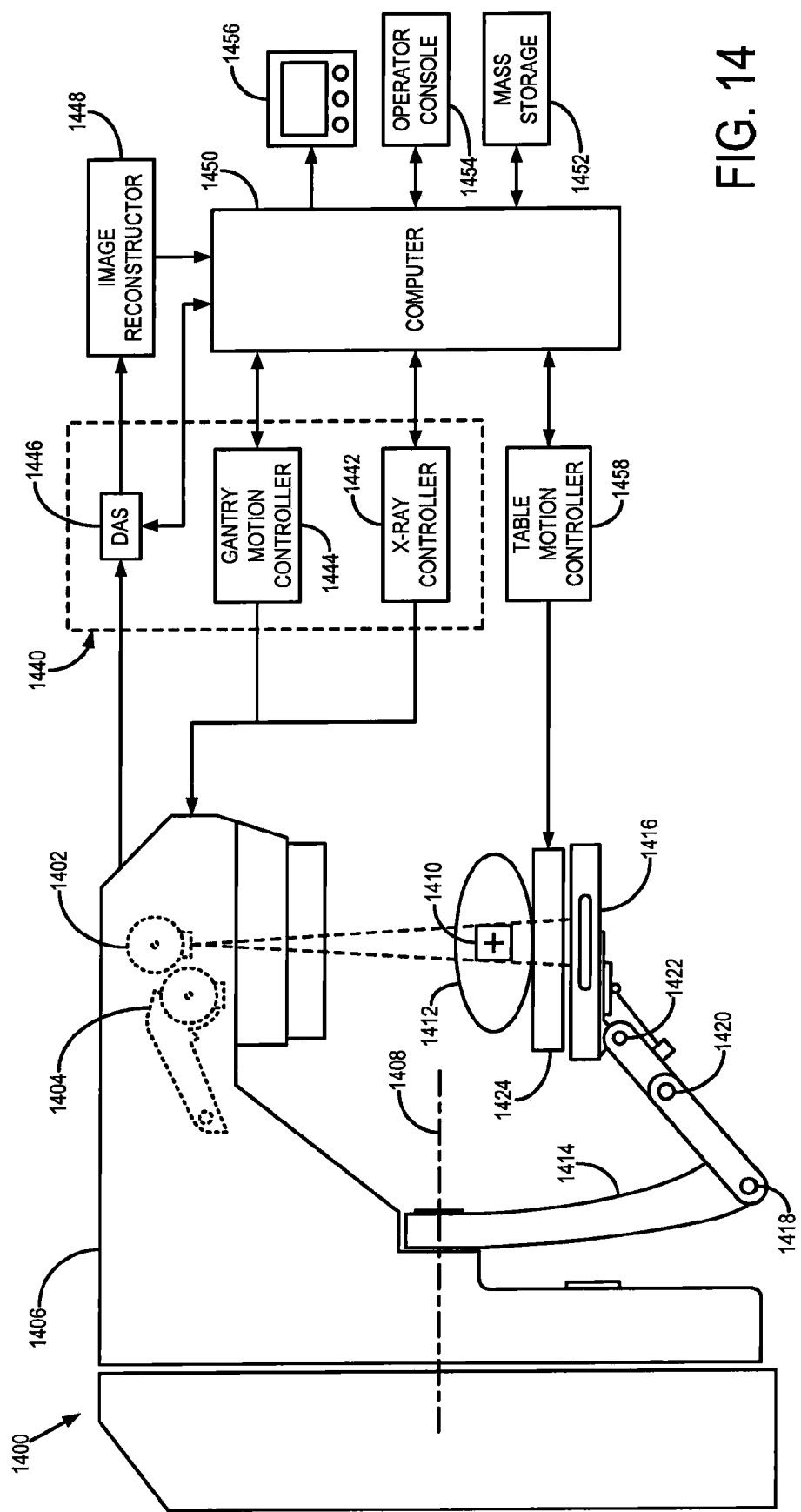
FIG. 14 is a block diagram of an exemplary image-guided radiation therapy (IGRT) system, which employs yet another embodiment of the present invention.

With initial reference to FIG. 14, an image-guided radiation therapy (IGRT) system 1400 includes a therapeutic x-ray source 1402 and a diagnostic x-ray source 1404. The diagnostic x-ray source 1404 projects a cone-beam of x-rays toward a detector array 1416. Both the therapeutic x-ray source 1402 and diagnostic x-ray source 1404 are attached adjacent each other and housed at the same end of a first rotatable gantry 1406, which rotates about a pivot axis 1408. The first rotatable gantry 1406 allows either of the x-ray sources, 1402 and 1404, to be aligned in a desired manner with respect to a target volume 1410 in a subject 1412 positioned on a patient table 1424. A second rotatable gantry 1414 is rotatably attached to the first rotatable gantry 1406 such that it too is able to rotate about the pivot axis, 1408. Disposed on one end of the second rotatable gantry 1414 is an x-ray detector 1416. The x-ray detector 1416 functions not only as a diagnostic image device when receiving x-rays from the diagnostic x-ray source 1404, but also as a portal image device when receiving x-rays from the therapeutic x-ray source 1402. The detector array 1416 is formed by a number of detector elements that together sense the projected x-rays that pass through the subject 1412. Each detector element produces an electrical signal that represents the intensity of an impinging x-ray beam and, hence, the attenuation of the beam as it passes through the subject 1412. The second rotatable gantry 1414 further includes an articulating end that can pivot about three points 1418, 1420, and 1422. The pivoting motion provided by these points 1418, 1420, and 1422, allows the x-ray detector 1416 to be moved within a two-dimensional plane.

The rotation of the rotatable gantries, 1406 and 1414, and the operation of the x-ray sources, 1402 and 1404, are governed by a control mechanism 1440 of the IGRT system. The control mechanism 1440 includes an x-ray controller 1442 that provides power and timing signals to the x-ray sources, 1402 and 1404, and a gantry motor controller 1444 that controls the rotational speed and position of the gantries, 1406 and 1414. A data acquisition system (DAS) 1446 in the control mechanism 1440 samples analog data from detector elements and converts the data to digital signals for subsequent processing. An image reconstructor 1448, receives sampled and digitized x-ray data from the DAS 1446 and performs high speed image reconstruction. The reconstructed image is applied as an input to a computer 1450 which stores the image in a mass storage device 1452.

The computer 1450 also receives commands and scanning parameters from an operator via a console 1454 that has a keyboard. An associated display 1456 allows the operator to observe the reconstructed image and other data from the computer 1450. The operator supplied commands and parameters are used by the computer 1450 to provide control signals and information to the DAS 1446, the x-ray controller 1442 and the gantry motor controller 1444. In addition, the computer 1450 operates a table motor controller 1458 which controls the motorized patient table 1424 to position the subject 1412 within the gantries, 1406 and 1414.

Image Reconstruction in an IGRT System

In yet another embodiment of the present invention, the image reconstruction method described above with reference to FIG. 11 is employed to improve the accuracy of radiation delivered during a treatment session. More specifically, and as will be described below in detail, a correction image is produced and employed to produce a "prior image" for a PICCS image reconstruction method, such as the one described, for example, in co-pending U.S. patent application Ser. No. 12/248,590.

Figure 15:
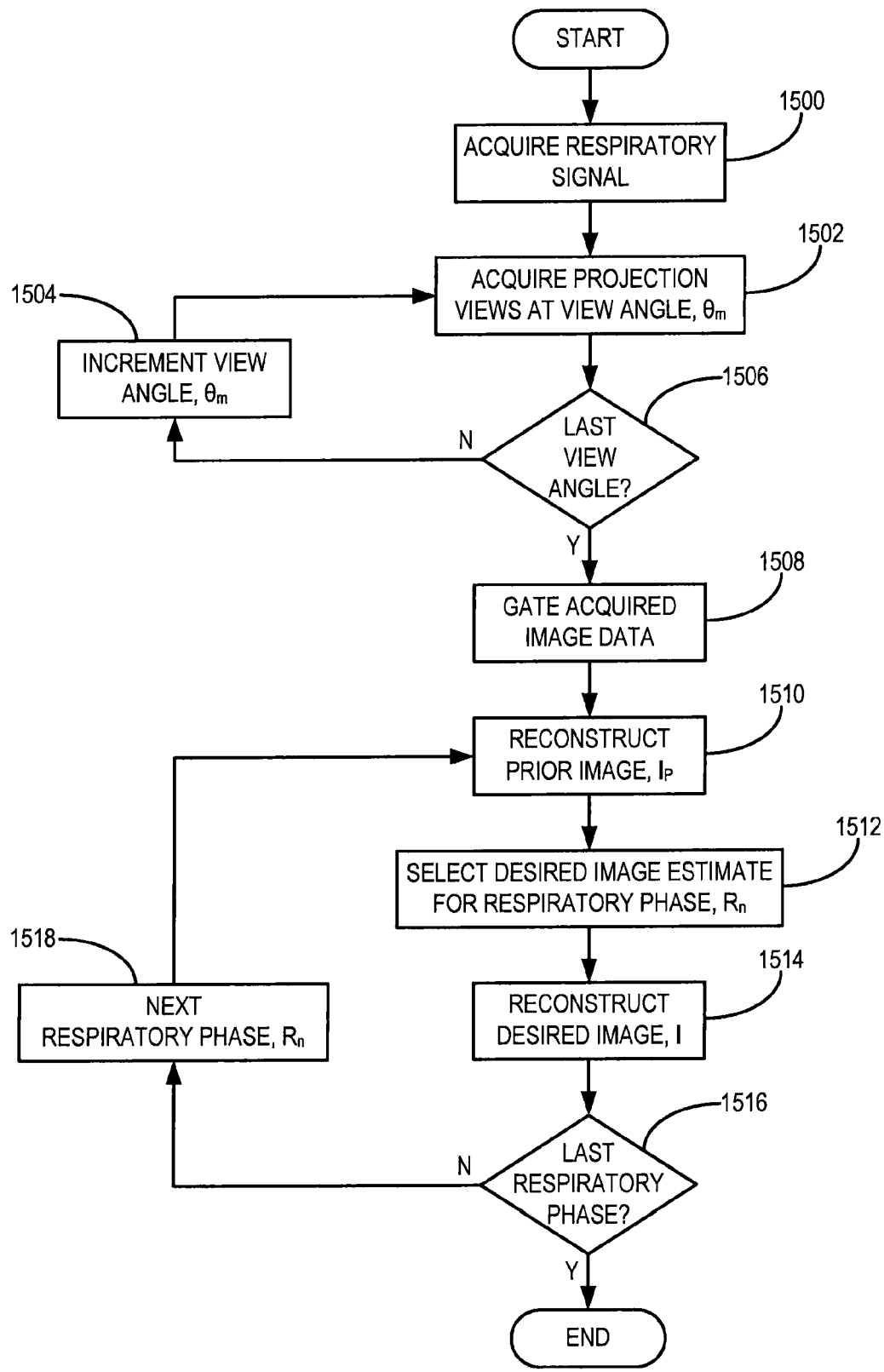
FIG. 15 is a flowchart of yet another embodiment of the present invention using the IGRT system of FIG. 14.

An image-guided radiation therapy system, such as the one described above with reference to FIG. 14 can be employed to practice an embodiment of the present invention. Referring now particularly to FIG. 15, the method of the aforementioned embodiment starts by acquiring a signal indicative of respiratory motion in the subject, as indicated at step 1500. Such a signal is acquired using a respiration monitoring device such as a spirometer, a respiratory bellows, or a respiratory motion tracking system. An exemplary respiratory motion tracking system is the system commercially available under the trade name "Real-time Position Management™" (Varian Medical Systems, Palo Alto, Calif.). This respiratory motion signal is later used to gate the acquired x-ray image data into N different respiratory phases, $R_n$. Data acquisition subsequently begins by acquiring x-ray image data in the form of a set of projection views at a first view angle, $\theta_m$, as indicated at step 1502. The diagnostic x-ray source 1404 and detector 1416 are subsequently rotated to a new view angle at step 1504, where image data is again acquired. This process is repeated until the diagnostic x-ray source 1404 and detector 1416 have been rotated to a last view angle, $\theta_M$, as indicated by decision block 1506.

After all of the image data has been acquired, the reconstruction process begins. The acquired x-ray image data is subsequently gated into the N different respiratory phases, $R_n$, was indicated at step 1508. For example all of the image data acquired during a first gating window, $W_1$, is selected as corresponding to a first respiratory phase, $R_1$. This retrospective gating produces a "respiratory phase image data set" for each of the N different desired respiratory phases. Therefore, each respiratory phase image data set includes a plurality of projection views acquired during the gating window, $W_n$, corresponding to a given respiratory phase, $R_n$. In the alternative, the original image data acquisition can be prospectively gated such that image data is only acquired at specific time points during the respiratory signal. Following this data acquisition scheme, all of the image data acquired during a selected respiratory phase is similarly combined into a respiratory phase image data set.

A prior image, $I_P$, is reconstructed next, as indicated at step 1510. In general, the prior image, $I_P$, is reconstructed using a method that includes information in the desired respiratory phase image that is to be reconstructed. One embodiment of such a method is described above with respect to FIG. 11, in which a prior image, $I_P$, is reconstructed for each respiratory phase. In general, the available data for a specific respiratory phase is very limited. For example, only about 20 projection view angles may be included in a given respiratory phase image data set. Since each respiratory phase image data set is highly undersampled, an attempt to reconstruct images using standard image reconstruction algorithms, such as the well-known filtered backprojection (FBP) method, will result in severe streaking and distortion artifacts. In order to reconstruct a high quality image, a first respiratory phase, $R_n$, is selected at step 1512. As indicated next at step 1514, a desired image, I, of the selected respiratory phase, $R_n$, is subsequently reconstructed using a method that utilizes, in part, the reconstruction methods described above with reference to FIGS. 1, 2, and 3.

A desired image, I, is reconstructed for each respiratory phase, $R_n$, in this manner until an image for all of the desired respiratory phases has been reconstructed, as decided at process block 1516. If all of the desired images have not been reconstructed, a next respiratory phase, $R_n$, is selected at step 1518 and the above described image reconstruction method is repeated. By utilizing the aforementioned image reconstruction method, information corresponding to each respiratory phase is included in the prior image used when reconstructing each individual respiratory phase image. In this manner, a time series of images that more accurately depicts a subject's respiratory motion is produced. From this time series of images, the motion characteristics of a tumor in response to a subject's respiration are determined. Using these motion characteristics, the radiation delivery plan for a treatment session can be accordingly adjusted so that a reduced dose of radiation is imparted to healthy tissue while escalating the dose to the tumor.

The present invention has been described in terms of one or more preferred embodiments, and it should be appreciated that many equivalents, alternatives, variations, and modifications, aside from those expressly stated, are possible and within the scope of the invention. It should be appreciated by those skilled in the art that there are many variations possible from the particular embodiments described above. For example, it should be appreciated by those skilled in the art that equations (19) and (20) can be modified such that a plurality of sparsifying images are employed to determine a corresponding plurality of correction images.

The invention claimed is:

1. A method for producing an image of a subject positioned in a field of view (FOV) of a medical imaging system, the steps comprising:
   a) acquiring, with a motion monitoring system, a signal indicative of motion in the subject;
   b) acquiring, with the medical imaging system, a plurality of image data sets of the subject positioned in the FOV at a corresponding plurality of time frames;
   c) reconstructing a sparsifying image by combining data from the plurality of acquired image data sets;
   d) producing a sparsifying image data set by transforming the sparsifying image reconstructed in step c);
   e) producing a difference image data set by subtracting the image data set acquired in a selected time frame from the sparsifying image data set produced in step d), wherein the selected time frame is selected using the signal indicative of motion in the subject acquired in step a);
   f) reconstructing a correction image using the difference image data set produced in step e); and
   g) subtracting the correction image from the sparsifying image reconstructed in step c) to produce an image of the subject at the selected time frame.

2. The method as recited in claim 1 in which step d) includes regridding the sparsifying image to a sampling pattern of the image data set acquired at a selected time frame.

3. The method as recited in claim 1 in which the medical imaging system is an x-ray computed tomography (CT) imaging system and the image data sets acquired in step a) are interleaved x-ray projection space data sets.

4. The method as recited in claim 1 in which the plurality of image data sets acquired in step a) include undersampled image data sets.

5. The method as recited in claim 1 in which the medical imaging system is an image-guided radiation therapy (IGRT) system and the image data sets acquired in step b) are x-ray projection space data sets.

6. The method as recited in claim 5 in which:
   the motion monitoring systems includes a respiration monitoring device;
   the acquired signal indicative of motion in the subject is a signal indicative of respiratory motion in the subject; and further including:
   h) reconstructing an image of the subject using a PICCS image reconstruction method.

7. The method as recited in claim 6 in which step e) includes producing a respiratory phase image data set from the plurality of image data sets acquired in step a) using the acquired signal indicative of respiratory motion.

8. The method as recited in claim 7 in which the correction image produced in step f) is indicative of a respiratory phase and step h) includes using the image reconstructed in step g) as a prior image.

9. The method as recited in claim 7 further including:
   i) updating a radiation delivery plan using the image reconstructed in step h).

* * * * *

UNITED STATES PATENT AND TRADEMARK OFFICE
CERTIFICATE OF CORRECTION

| | | |
|---|---|---|
| PATENT NO. | : 8,229,199 B2 | Page 1 of 1 |
| APPLICATION NO. | : 12/341598 | |
| DATED | : July 24, 2012 | |
| INVENTOR(S) | : Guang-Hong Chen et al. | |

It is certified that error appears in the above-identified patent and that said Letters Patent is hereby corrected as shown below:

Col. 1, Lines 22-25 should be replaced with the following: -- This invention was made with United States government support awarded by the following agencies: NIH EB005712 and EB007021. The United States government has certain rights in this invention. --

Col. 5, Line 47, "$\alpha\sqrt{0.3}$-0.7" should be -- $\alpha \approx 0.3$ --

Signed and Sealed this
Eleventh Day of September, 2012

David J. Kappos
*Director of the United States Patent and Trademark Office*